(12) United States Patent  
Schlesinger et al.

(10) Patent No.: US 7,726,177 B2
(45) Date of Patent: Jun. 1, 2010

(54) ENVIRONMENTAL HAZARD SENSOR

(75) Inventors: Morton Lee Schlesinger, Bloomington, MN (US); Anthony Charles Young, Maple Grove, MN (US); John Dee King, Roseville, MN (US)

(73) Assignee: Detector Electronics Corporation, Minneapolis, MN (US)

( * ) Notice: Subject to any disclaimer, the term of this patent is extended or adjusted under 35 U.S.C. 154(b) by 526 days.

(21) Appl. No.: 11/715,252

(22) Filed: Mar. 6, 2007

(65) Prior Publication Data

US 2008/0216553 A1 Sep. 11, 2008

(51) Int. Cl.
*G01N 19/10* (2006.01)
(52) U.S. Cl. .................................... 73/31.02
(58) Field of Classification Search ........................ None
See application file for complete search history.

(56) References Cited

U.S. PATENT DOCUMENTS 6,336,354 B1 * 1/2002 Suzuki et al. .............. 73/31.05
6,467,334 B2 * 10/2002 Lloyd et al. ................ 73/31.06

* cited by examiner

*Primary Examiner*—Robert R Raevis
(74) *Attorney, Agent, or Firm*—Kinney & Lange, P.A.

(57) ABSTRACT

An apparatus for sensing a constituent in an environment including a sensor circuit and a suppression circuit. The sensor circuit has a sensor element and an operating state control element. The sensor element senses the constituent by presenting an electrical parameter which varies as a function of a degree of the constituent. The control element maintains the sensor at a preferred operating state. A detected electrical parameter of said sensor element is subject to error resulting from a leakage of electrical current between the control element and the sensor element. The suppression circuit reduces or stops the leakage to reduce the error.

19 Claims, 27 Drawing Sheets

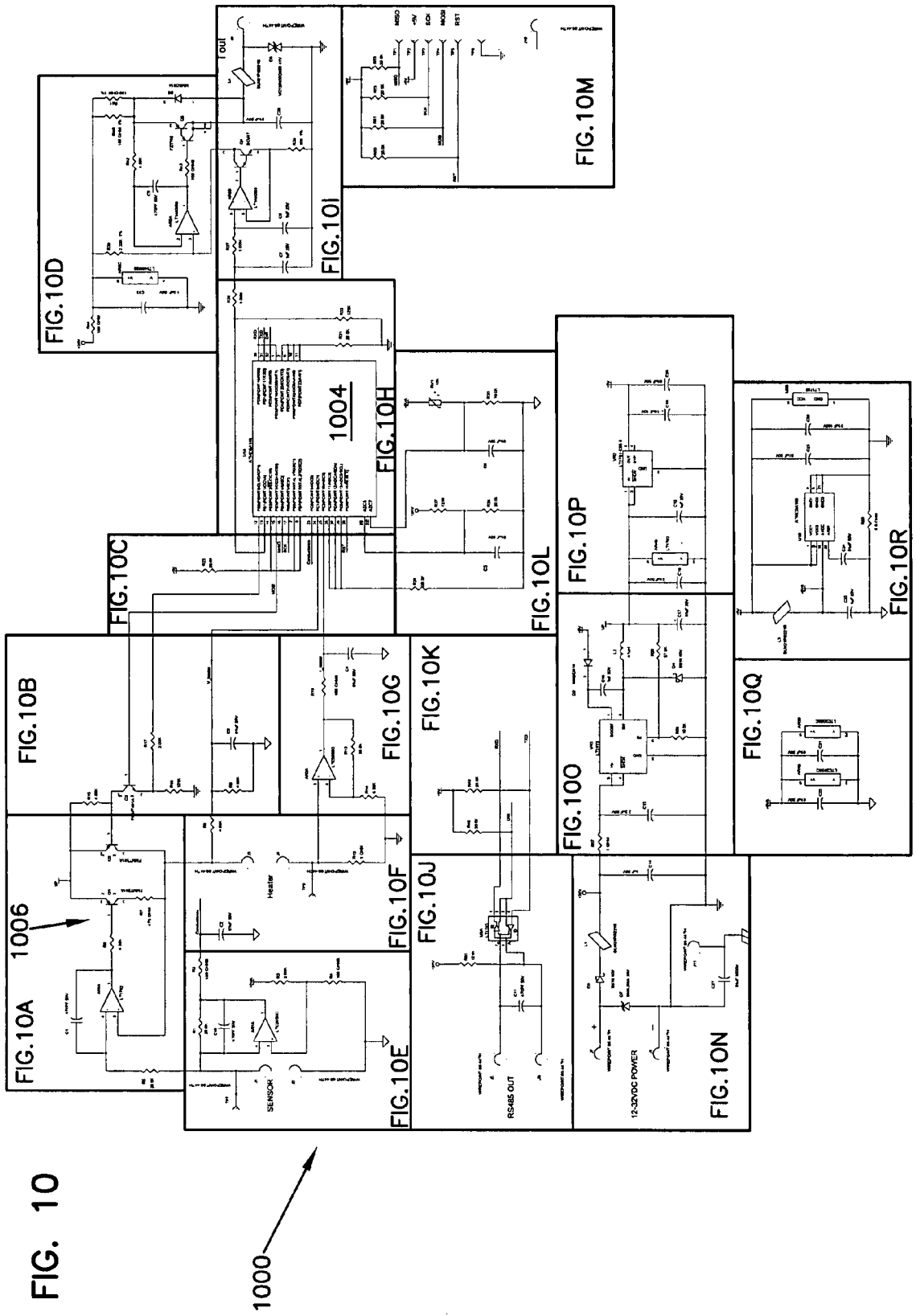

FIG. 10F
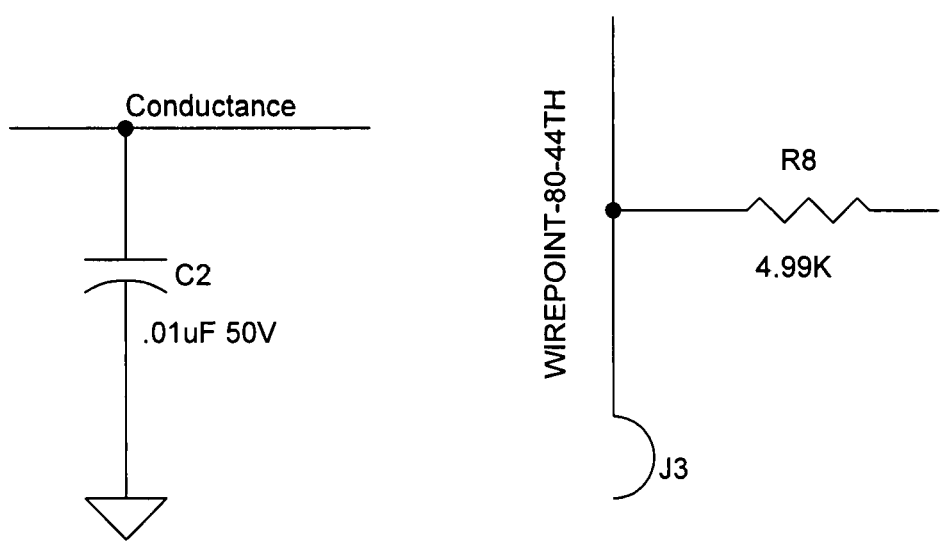
Heater
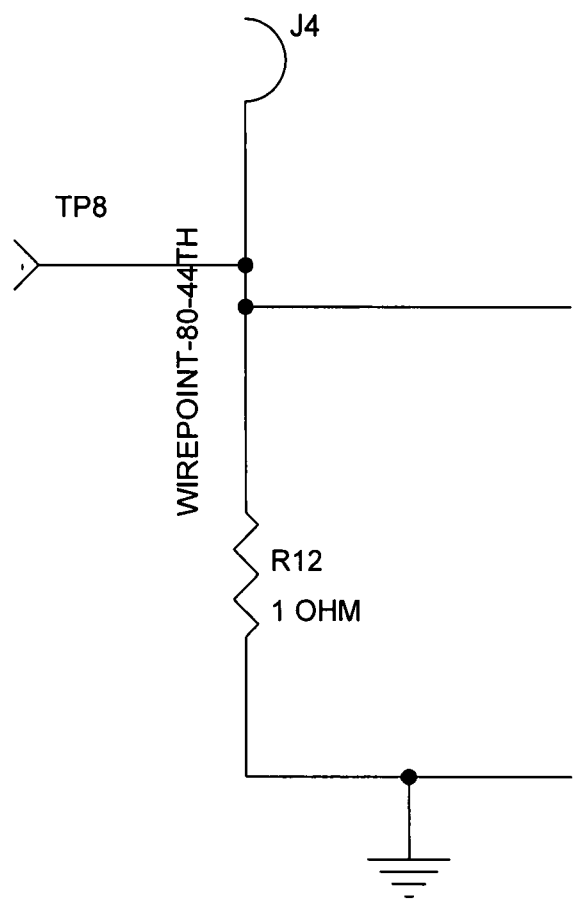

FIG. 10M
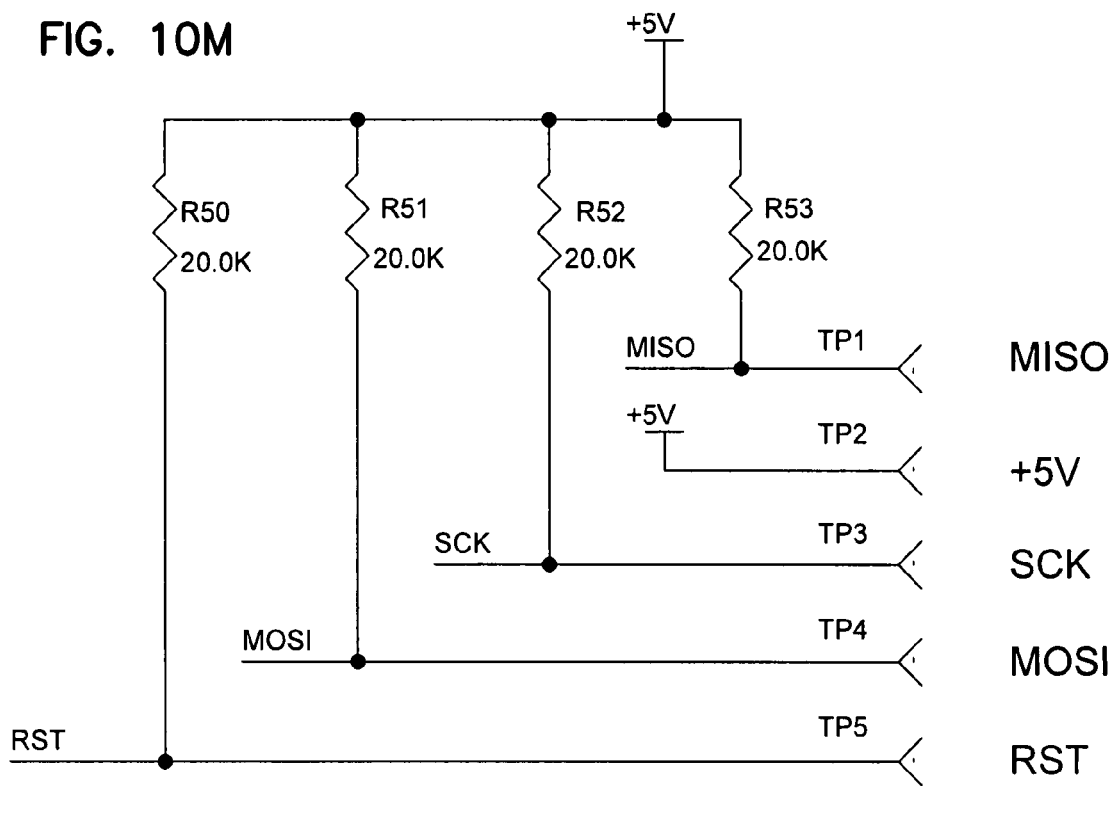

ENVIRONMENTAL HAZARD SENSOR

I. BACKGROUND OF THE INVENTION

1. Field of the Invention

The present invention relates to methods and apparatus for sensing environment hazards (e.g., a toxic gas). More particularly, this invention pertains to such hazard detection with a suppression circuit for inhibiting (i.e., reducing or eliminating) stray electrical current from associated equipment in proximity to the sensor to mitigate sensing errors.

2. Description of the Prior Art

As will be described, the present invention is preferably used for sensing environmental hazards in ambient air. For example, the present invention senses for toxic gases.

Toxic gases are a common risk associated with oil well drilling. Notably, such drilling can result in release of hydrogen sulfide, which is highly toxic. As a result, drill sites will be provided with one or more sensors for sensing the presence and concentration of hydrogen sulfide in ambient air.

Common prior art sensors for sensing hydrogen sulfide are so-called electro-chemical sensors. While such electrochemical sensors enjoy a reputation for accuracy, they are not without operational limitations. For example, such electro-chemical sensors are sensitive to environmental conditions. Namely, in hot and dry environments (common to many oil drilling facilities in arid locations), the sensors may dry out and become non-functional. In extremely cold environments, the sensors may freeze.

In addition to their environmental limitations, electro-chemical sensors have other potential limitations. For example, they are relatively slow in responding to changes in concentration of the gas being sensed. Also, they have a relatively short useful life.

Solid state sensors have been used as alternatives to electrochemical sensors. So-called metal oxide semiconductor (MOS) sensors can detect environmental hazards (e.g., hydrogen sulfide). An example of such an MOS sensor is Product No. S4000T (Intelligent Sensor) of General Monitor, 26776 Simpatica Circle, Lake Forest, Calif., USA. Another such sensor is an MOS sensor (Product No. 714) of Synkera, 2021 Miller Dr., Suite B., Longmont, Colo., USA.

Such MOS sensors have an electrical resistance which varies in response to the environmental hazard. For example, the sensor's resistance can vary in response to the concentration of hydrogen sulfide in ambient air. For example, by measuring this resistance, the amount of the sensed hazard can be computed. The resistance of an MOS sensor can be indirectly measured by measuring a voltage drop across the sensor (or current flow through the sensor).

Solid state sensors are not as susceptible to many of the environmental limitations of electro-chemical sensors (e.g., drying out in hot and dry environments). They also are rapid, durable and enjoy a relatively long operating life.

Notwithstanding their benefits, solid state sensors can present operational challenges of their own. For example, their accuracy can vary with changes in humidity and temperature.

To maintain accuracy, solid state sensors may be provided with an electrical resistance heating element to maintain the sensor at a desired operating temperature. For example, some MOS sensors perform with greatest accuracy when heated to about 300° C. Commonly, the resistive heating element is in direct contact with the solid state sensor for rapid conductive heating of the sensor by the heating element. The temperature of the sensor then can be indirectly determined by measuring the resistance of the heating element or the output of another temperature sensing device. Current to the heating element is altered to maintain the heating element (and, hence the sensor) at a desired operating temperature within tolerances which may vary from application to application.

While the foregoing maintains the sensor at desired operating temperatures when implemented in accordance with suggestions of the sensor's manufacturer, other problems arise. Namely, an undesired leakage of electrical current can develop between the sensor circuit and the heater circuit (e.g., through a heated dielectric or through impurities in the dielectric). The amount of such current is not easily determinable and can vary widely from application-to-application and over time. This leaked current can result in a false reading of the resistance of the sensor resulting in an erroneous interpretation of the degree of presence of the environment hazard of interest.

II. SUMMARY OF THE INVENTION

According to a preferred embodiment of the present invention, a method and apparatus are disclosed for sensing a constituent in an environment. The apparatus includes a sensor circuit and a suppression circuit. The sensor circuit has a sensor element and an operating state control element. The sensor element senses the environmental constituent by presenting an electrical parameter which varies with the constituent. The sensor also has a preferred operating state. The control element maintains the sensor at a preferred operating state. Detection and processing of the electrical parameter of the sensor element is subject to error resulting from a leakage of electrical current between the control element and the sensor element. The suppression circuit mitigates the current leak to reduce the error.

In a most preferred embodiment, the sensor element has an electrical resistance which varies in response to a gas in ambient air. The control element is a heating element for maintaining the sensor element at a preferred operating temperature. The suppression circuit includes circuit components to alternate between providing an operating current (i.e., sufficient current to operate the heating element) to the heating element and driving the heating element to the same potential as the sensor element. The resistance of the sensor element is measured when the suppression circuit drives the heating element. The resistance is not measured when the operating current is provided to the heating element

III. BRIEF DESCRIPTION OF THE DRAWINGS

FIGS. 10(A-R) are larger views of portions of the wiring diagram of FIG. 10 as delineated in FIG. 10.

IV. DETAILED DESCRIPTION OF THE PREFERRED EMBODIMENTS

Referring now to the several drawing Figures in which identical elements are numbered identically throughout, a description of a preferred embodiment of the present invention will now be provided. In the preferred embodiment, the invention is described with reference to use of a solid state sensor for sensing the concentration of hydrogen sulfide in ambient air. The sensing apparatus includes a suppression circuit for inhibiting undesired current leakage between the sensor and a heating element provided to maintain the sensor at a desired operating temperature. It will be appreciated the teachings of the present disclosure could be applied to any apparatus for sensing an environmental constituent where a reading of the sensor is subject to error resulting from current leakage between the sensor and a device for maintaining the sensor at a desired operating state.

Figure 1:
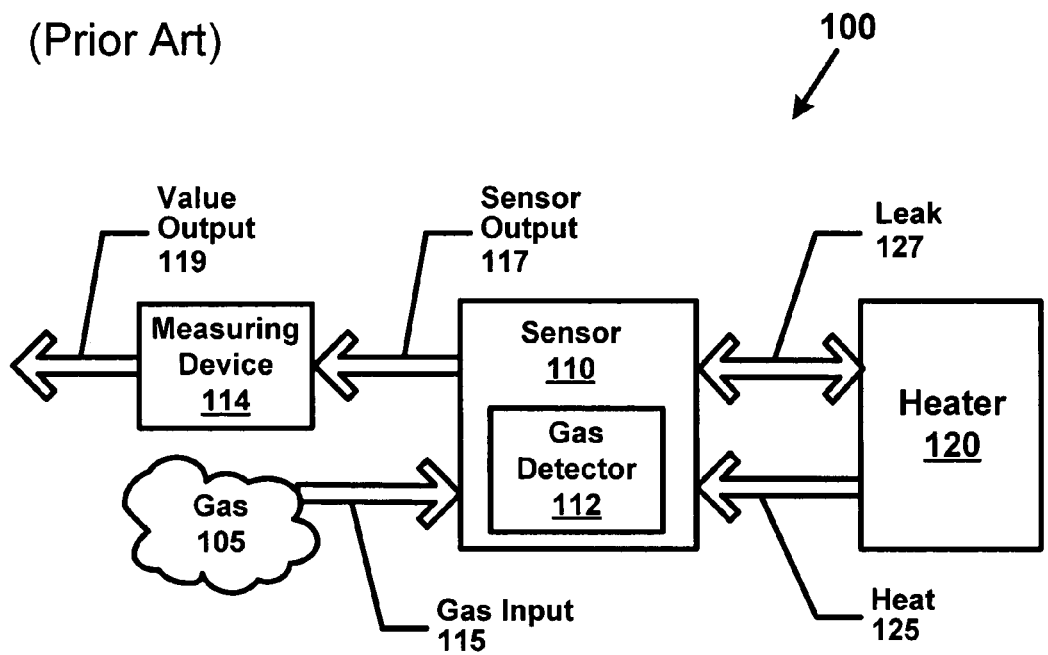
FIG. 1 is a block diagram of a solid state sensor in combination with a heating element according to the prior art and illustrating a current leakage between the heating element and the sensor.
Figure 2:
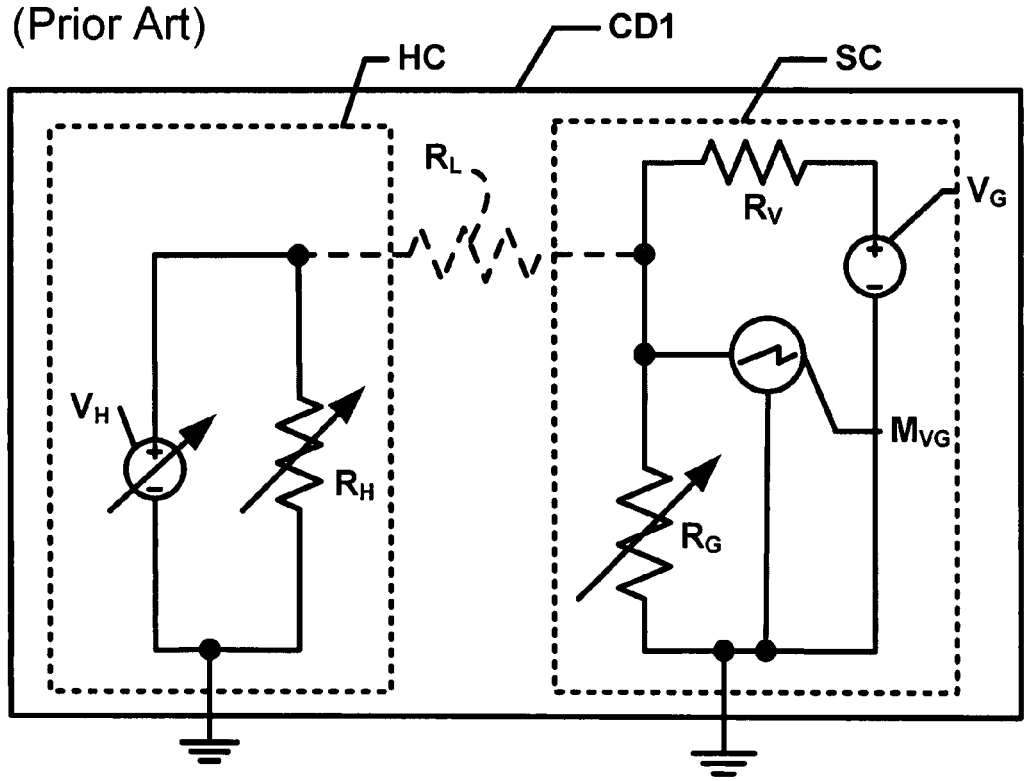
FIG. 2 is a simplified electrical schematic wiring diagram illustrating the solid state sensor of FIG. 1.

FIGS. 1 and 2 illustrate one of the problems in the prior art. FIG. 1 illustrates a sensor system 100 including a hydrogen sulfide sensor element 110, such as an MOS sensor described above. In general, the sensor element 110 is configured to receive input 115 (e.g., a gas suspected of containing a hazardous substance or other substance of interest), to determine whether a particular substance is contained in the input 115 using a detection device 112, and to output an indication (e.g., a resistance or associated voltage drop) 117 of the presence or absence of the substance. Typically, the sensor element 110 cooperates with a measuring device 114 configured to determine the amount of the substance contained in the input 115 and to output a measurement value 119 (e.g., indicating a hazardous gas concentration).

As noted above, some conventional solid-state sensors must be heated at elevated temperatures to function accurately and/or efficiently. The sensor element 110 of FIG. 1 is coupled to a heater 120 to maintain the sensor element 110 at a predetermined temperature range. For example, the heater 120 can maintain the temperature of a solid-state, hydrogen-sulfide sensor element 110 at about 300° C. plus or minus about 50° C. Generating heat (see path 125 of FIG. 1) requires passing a large amount of current through the heater 120. Some of this current can leak (see path 127 of FIG. 1) to the sensor element 110 and interfere with detection of the environmental constituent.

Such leakage can be seen best in an electrical schematic diagram CD1 (FIG. 2) of the sensor system 100. In FIG. 2, leakage (indicated in phantom lines at $R_L$) can occur between a sensing circuit SC and a heater circuit HC. Generally, the sensing circuit SC includes a sensor element $R_G$ having a resistance. Typically, the sensor element $R_G$ is a variable resistor having a resistance that varies in response to the concentration of the environmental constituent (e.g., hydrogen sulfide) in the ambient air surrounding the sensor element $R_G$.

The sensing circuit SC also includes a fixed voltage source $V_G$ and a resistor $R_V$ in series connection to permit measurement of a voltage drop across the sensor element $R_G$ with a meter $M_{VG}$. The measured voltage drop is an indirect measurement of the resistance of the sensor element $R_G$ from which the concentration of the constituent can be computed.

The sensor element $R_G$ has greatest efficacy when maintained at a desired operating temperature. To maintain this temperature, a heating circuit HC is provided. The heating circuit HC includes an electrically resistive heating element represented by resistor $R_H$. Typically, the heating element $R_H$ is a flat, electrically conductive strip lying on a surface of the sensor element $R_G$. The heating element $R_H$ conductively heats the sensor element $R_G$ as the temperature of the heating element $R_H$ increases in response to current flow through the heating element $R_H$. A voltage source $V_H$ supplies power to the heating element $R_H$.

Since the heating element $R_H$ is arranged adjacent the solid state sensor element $R_G$, current can flow from the heating circuit HC to the sensing circuit SC. For example, when a dielectric separating the heating circuit HC from the sensing circuit SC heats up, the conductivity of the dielectric can increase. Impurities in the dielectric also can result in current flow between the circuits SC, HC. This current flow is represented by the dashed pathway with resistance $R_L$. The leakage current can alter the measured voltage drop across the sensor element $R_G$. This altered measurement can result in an erroneous calculation of the concentration of the constituent (e.g., hydrogen sulfide) in the environment.

The amount of leakage current flow $R_L$ is not readily determinable. The leakage flow $R_L$ can vary over time since the amount of current coursing through the heating element $R_H$ can be adjusted in response to changes in the ambient temperature in order to maintain the heating element $R_H$ at a target temperature. In addition, the leakage current can be a net forward flow (i.e., progressing from the heating circuit HC to the sensing circuit SC) or a net backward flow (i.e., progressing from the sensing circuit SC to the heating circuit HC).

Figure 3:
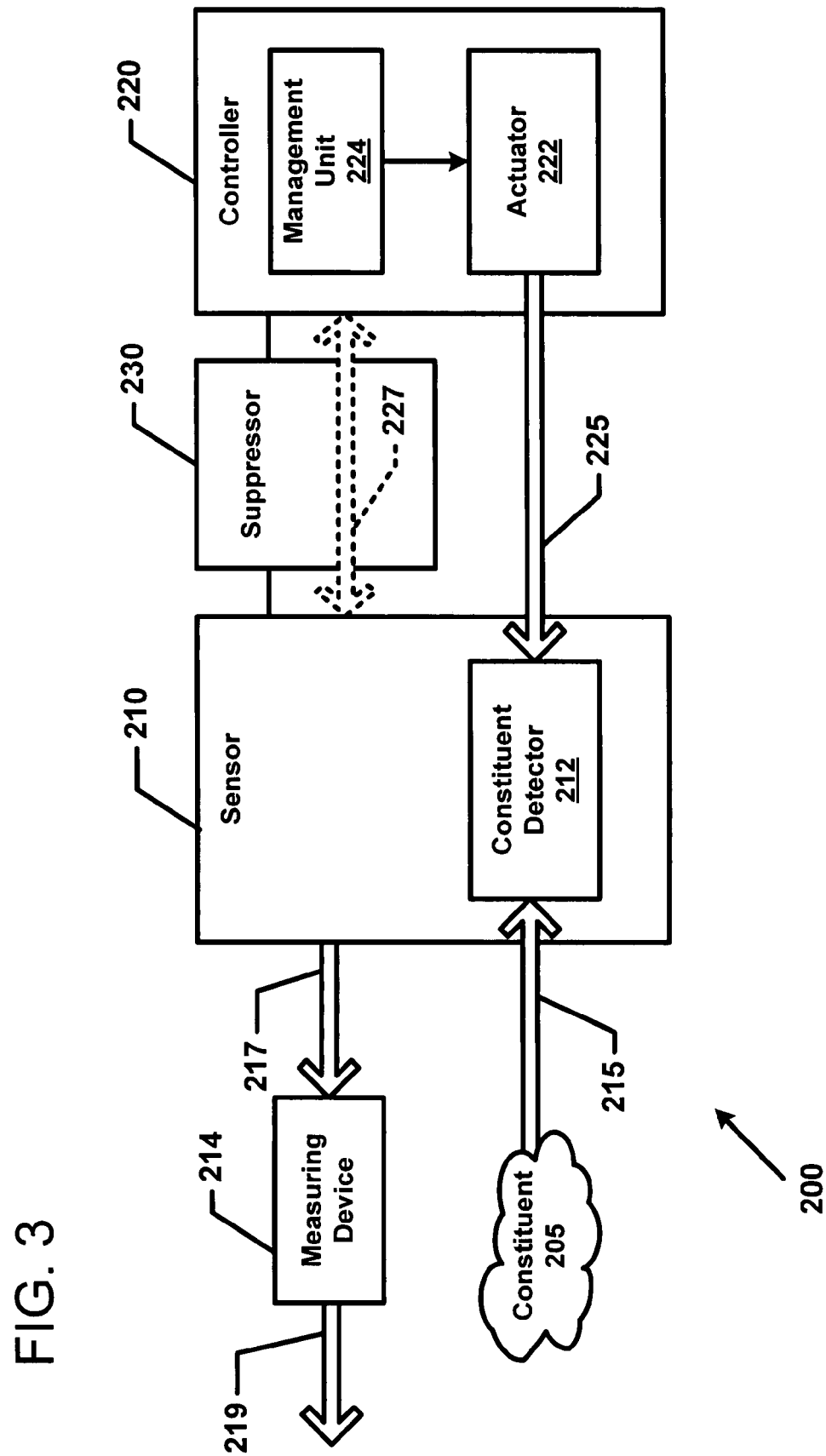
FIG. 3 is a block diagram of a solid state sensor in combination with a control element according to the principles of the present invention.

Having more thoroughly described the prior art and its deficiencies, the present invention and its benefits can be better appreciated with a description of a preferred embodiment which will now be described with reference to FIGS. 3-10. FIG. 3 is a block diagram generally illustrating a sensing system 200 including a sensor element 210, a controller 220, and a suppression element 230. The sensor element 210 is generally the same as the sensor element 110 of sensing system 100 (FIG. 1).

A controller 220 maintains at least one property of the sensor element 210 at a consistent operating state. For example, the controller 220 can regulate the temperature of the sensor element 210. In the example shown, the controller 220 includes an actuator 222 configured to adjust (represented at arrow 225) the operating state of the sensor element 210. The actuator 222 is controlled by a management unit 224. The management unit 224 determines when the actuator 222 acts (see 225) on the sensor element 210. For example, in a preferred embodiment, the actuator 222 is a heater and the management unit 224 controls when the heater provides heat to the sensor element 210.

The suppression element 230 reduces or prevents electrical current leakage (see phantom lines at 227) between the controller 220 and the sensor element 210. Although the example suppression element 230 shown in FIG. 3 is represented as a separate element, the suppression element 230 alternatively can be a component of either the sensor element 210 or the controller 220. The sensor element 210 and the controller 220 also need not be separate, spaced elements. In fact, in a preferred embodiment, the sensor element 210 and the controller 220 are arranged on a common circuit board.

Figure 4:
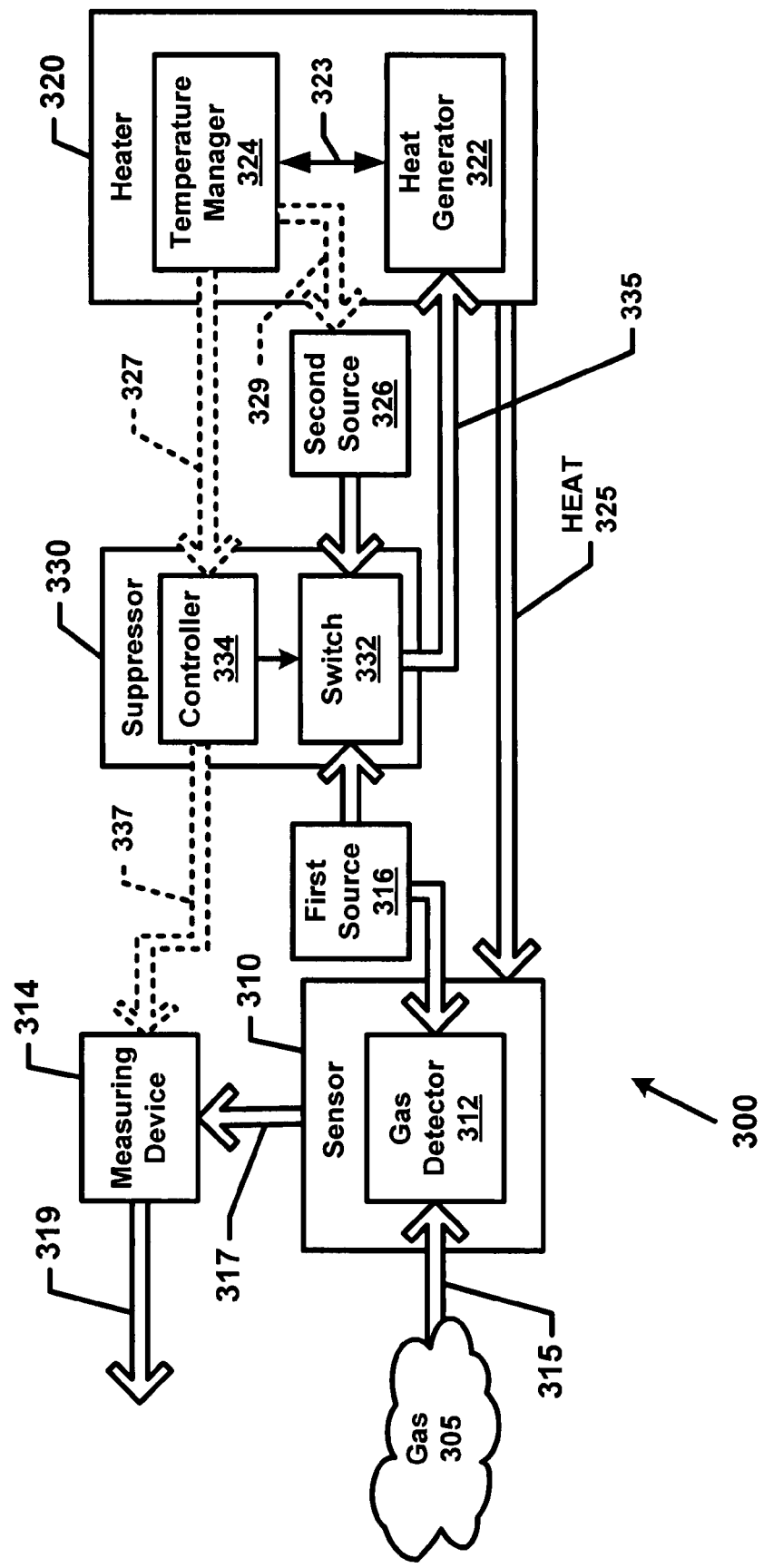
FIG. 4 is a block diagram depicting one exemplary embodiment of the solid state sensor of FIG. 3 in accordance with the principles of the present invention.

One exemplary sensing system 300 configured to reduce leakage is shown in detail in FIG. 4. The example sensing system 300 includes a sensor element 310, a heater element 320, and a suppression element 330. The sensor element 310 is the same as the sensor element 210 of FIG. 3 and is electrically coupled to a first power source (e.g., a voltage source) 316. The suppression element 330 also is electrically coupled to the first power source 316 and to a second power source (e.g., voltage source) 326. The second power source 326 typically operates at a significantly higher voltage than the first power source 316.

The heater element 320 is electrically connected to the suppression element 330, through which the heater element 320 receives power (see 335) from either the first power source 316 or the second power source 326. The heater element 320 includes a heat generator 322 and a temperature manager 324. The heat generator 322 is configured to emit heat when a voltage is applied across the heat generator 322. The temperature manager 324 is configured to control the heat generator 322 to regulate the amount of heat being produced.

In an example embodiment, the temperature manager 324 adjusts the amount of heat being produced by the heat generator 322 by monitoring (see arrow at 323) the heat level and communicating (see dashed lines at 327) with the suppressor 330 to electrically connect and electrically disconnect the heat generator 322 to and from the second power source 326 as appropriate. Typically, in such an embodiment, the second power source 326 applies a fixed voltage to the heat generator 322. The longer the voltage is applied to the heat generator 322, the hotter the heat generator 322 will become.

In another embodiment, the temperature manager 324 can modulate a heater element duty cycle in response to the amount of heat being generated. For example, the temperature manager 324 can activate and deactivate (see 323) the heat generator 322 according to the heater duty cycle. The heat generator 322 produces heat when activated and cools down when deactivated.

In yet another example embodiment, the temperature manager 324 adjusts the amount of heat being produced by modulating (see the dashed lines at 329) the voltage supplied by the second power source 326. In such an embodiment, the second power source 326 is a variable power source. For example, if additional heat is needed, then the temperature manager 324 increases the voltage provided by the second power source 326 to the heat generator 322. If the sensor element 310 is too warm, then the temperature manager 324 decreases the voltage provided by the second power source 326. Typically, in such an embodiment, the duty cycle according to which the voltage is applied to the heat generator 322 is kept constant.

The suppressor 330 reduces current flow between the gas detector 312 and the heat generator 322 by equalizing the voltage across the gas detector 312 and the heat generator 322. In the example shown, the suppression element 330 is electrically coupled to both the first power source 316 and the second power source 326. The suppressor 330 determines to which power source 316, 326 the heat generator 322 should be coupled at a given time. The suppressor 330 equalizes the voltage across the gas detector 312 and the heat generator 322 by temporarily coupling both the gas detector 312 and the heat generator 322 to the first power source 316. At such a time, the suppressor 330 also electrically disconnects the heat generator 322 from the second power source 326.

A controller 334 of the suppression element 330 signals (see 337) the measuring device 314 to gather data from the gas detector 312 when the voltage has been equalized. Such an arrangement is maintained for limited periods of time, however. Generally, the first power source 316 is not capable of producing enough current to generate sufficient heat to maintain the sensor element 310 at the target temperature. The heat generator 322, therefore, is reconnected to the second power source 326 before the temperature of the sensor element 310 is affected significantly.

In the example shown, the suppressor 330 includes a switch element 332 configured to couple the heat generator 322 of the heater element 320 alternately to the first power source 316 and to the second power source 326. The duty cycle of the switch element 332 (i.e., the ratio of time in which the switch is arranged in each position) is controlled by the suppressor controller 334. For example, the controller 334 can be a pulse-width-modulator or clock.

Figure 5:
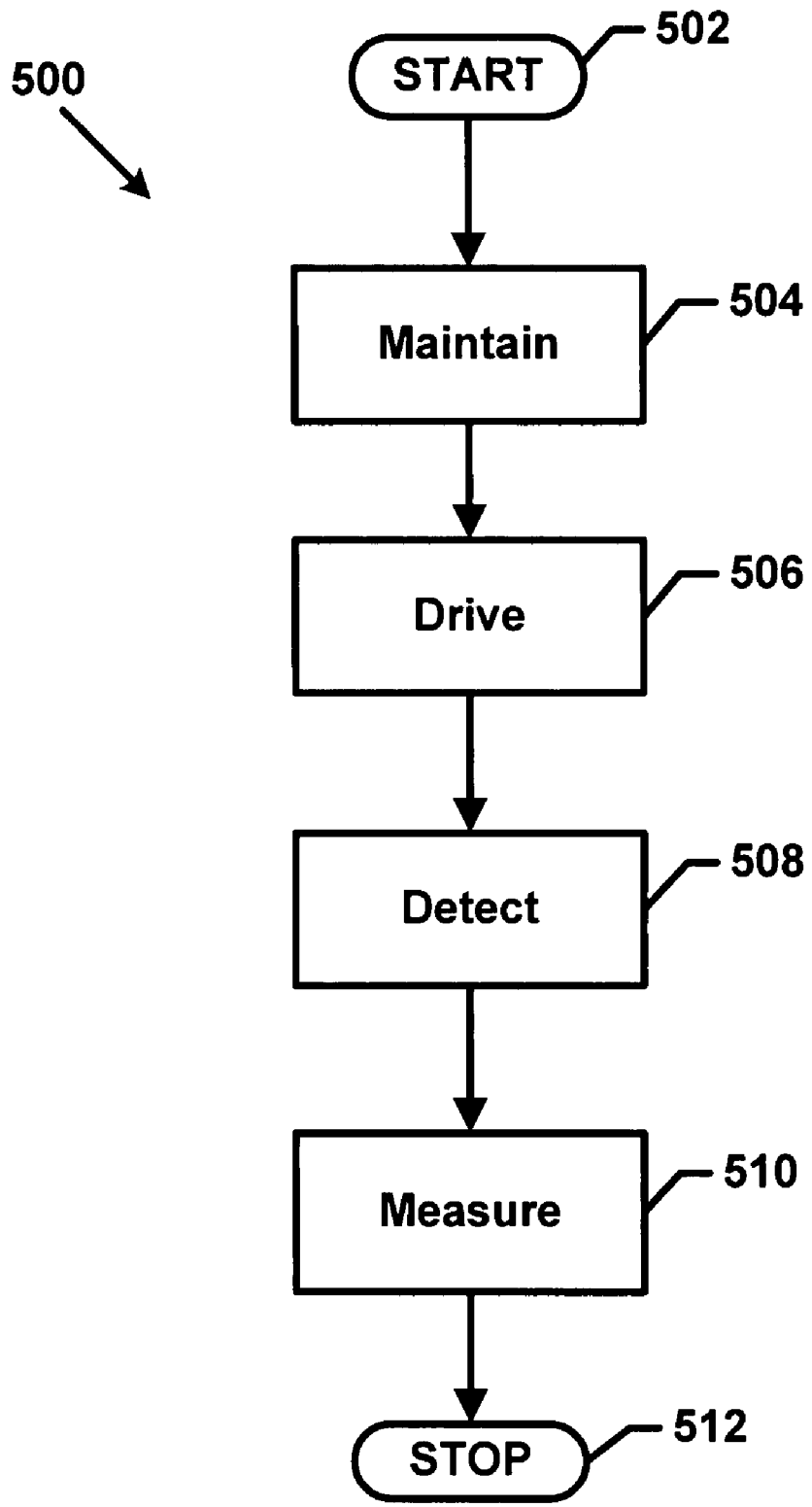
FIG. 5 is a flowchart illustrating an exemplary operational flow for using a sensing circuit to monitor the presence or absence of a gas, such as hydrogen sulfide, in accordance with the principles of the present invention.

The principles of the present invention can be best understood through an example application. FIG. 5 is a flow chart illustrating an exemplary operational flow for a sensing process 500 for using the sensing circuit 300 shown in FIG. 4 to monitor for the presence of an environmental constituent, such as hydrogen sulfide. The sensing process 500 initializes and begins at a start module 502 and proceeds to a maintain operation 504.

The maintain operation 504 operates the controller 334 of the suppressor 330 to maintain the operational state of the sensor element 310. In the example shown, the maintain operation 504 regulates the temperature of the sensor element 310 by signaling the suppressor controller 334 to adjust the duty cycle of the switch element 332. In other embodiments, however, other types of operational states can be regulated.

A drive operation 506 equalizes the voltages across the sensor element 310 and the heater element 320. For example, the drive operation 506 can operate the suppressor 330 to electrically couple the heater element 320 to the same power source as the sensor element 310.

A detect operation 508 determines whether a constituent, such as hydrogen sulfide gas, is present in a sample area, for example, air input into the sensor element 310 from the surrounding atmosphere. In the example shown in FIG. 4, the detect operation 508 monitors for a change in resistance of the sensor element 310 when the heat generator 322 is driven to the same voltage as the sensor element 310.

A measure operation 510 determines the amount of constituent present by measuring the change in resistance of the sensor element 310. For example, the measure operation 510 can infer the resistance of the sensor element 310 by measuring the voltage across the sensor element 310 and the current flowing through sensing circuit 300. The sensing process 500 cycles back to the maintain operation 504 to begin again as desired. The sensing process 500 completes and ends at stop module 512.

Figure 6:
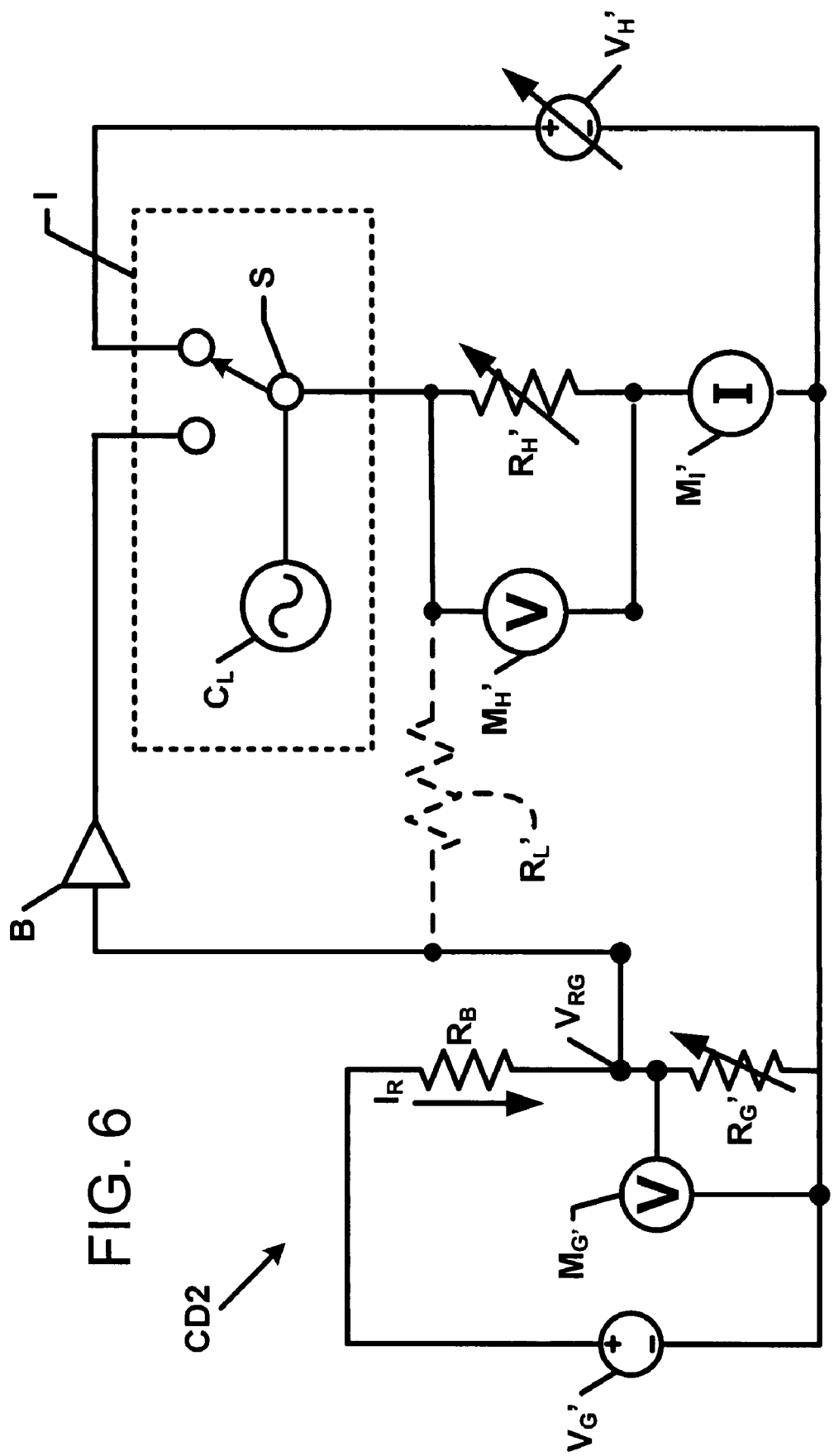
FIG. 6 is a simplified electrical schematic wiring diagram illustrating the solid state sensor of FIG. 4 arranged in a first configuration in accordance with the principles of the present invention.
Figure 7:
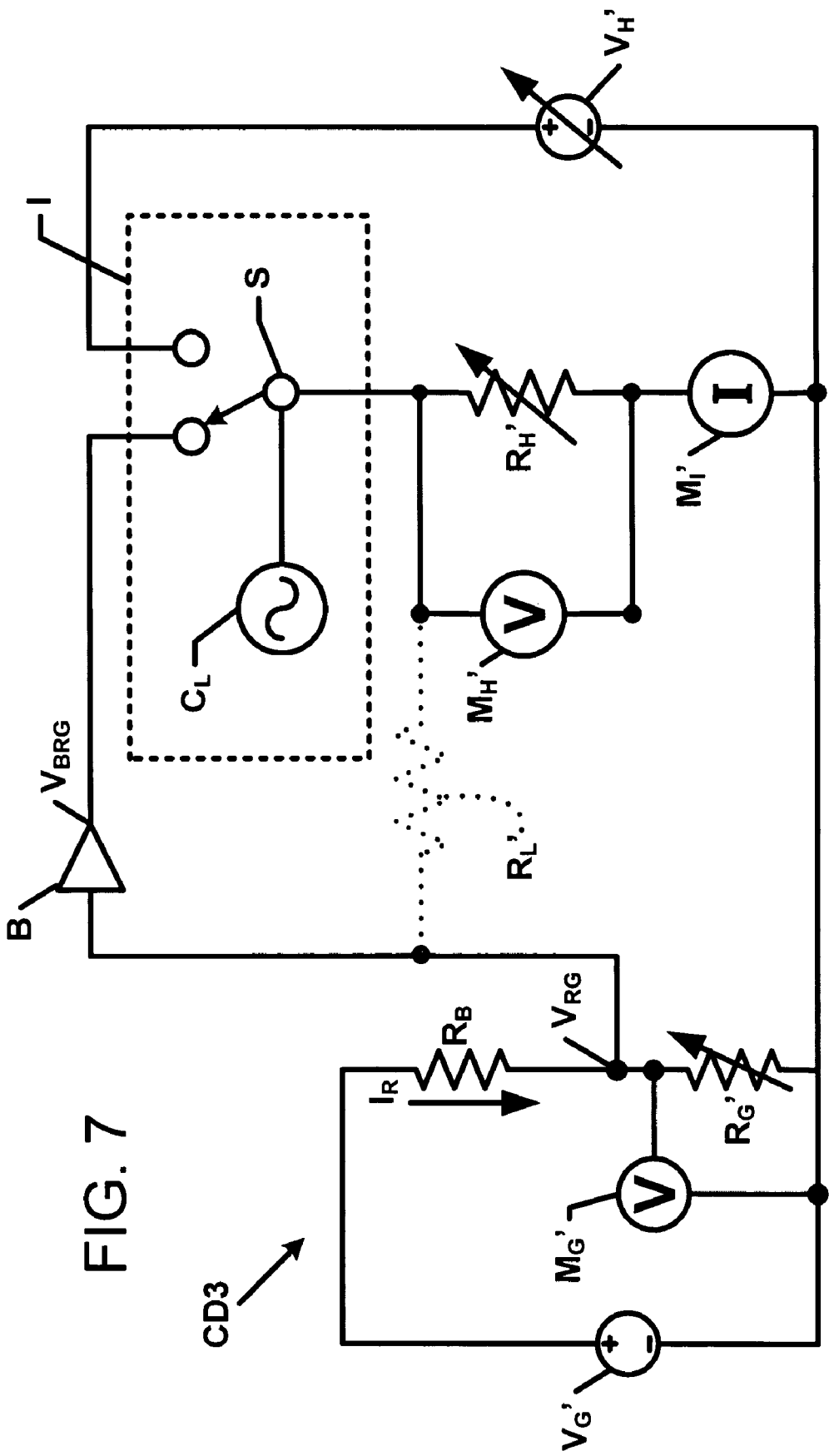
FIG. 7 is a simplified electrical schematic wiring diagram illustrating the solid state sensor of FIG. 4 arranged in a second configuration in accordance with the principles of the present invention.

FIGS. 6 and 7 are circuit diagrams $CD_2$, $CD_3$, respectively, illustrating an exemplary sensing circuit configured in accordance with the principles of the present invention. The first circuit diagram $CD_2$ illustrates the circuit arranged to regulate an operating temperature. The second circuit diagram $CD_3$ illustrates the circuit arranged to measure the quantity of constituent in the surrounding environment.

In the example shown, the circuit includes a first voltage source $V_G'$ that is typically a fixed voltage source. A sensing resistor $R_G'$ is arranged in a first complete circuit with the first voltage source $V_G'$. The sensing resistor $R_G'$ changes in resistance based on the amount of constituent to which the resistor $R_G'$ is exposed. A bias resistor $R_B$ is arranged within the first complete circuit to provide a voltage divider. A first measuring device $M_G'$ is electrically coupled to the sensing resistor $R_G'$ (e.g., in parallel) to measure an electrical parameter of the first complete circuit. For example, the first measuring device $M_G'$ can measure the voltage $V_{RG}$ across the sensing resistor $R_G'$.

The circuit also includes a second voltage source $V_H'$, which preferably can be either a fixed voltage source with time proportioned control or a variable voltage source with a constant duty cycle. In FIG. 6, the voltage source $V_H'$ forms a second complete circuit with a thermistor $R_H'$. The thermistor $R_H'$ produces heat when a current is run through the thermistor $R_H'$. Typically, the amount of heat produced varies in response to the amount of current run through the thermistor $R_H'$ and the amount of time over which the current is run.

A second measuring device (e.g., a voltmeter) $M_H'$ is electrically coupled to the thermistor $R_H'$ (e.g., in parallel) to measure an electrical parameter of the second complete circuit. For example, the second measuring device $M_H'$ can measure the voltage across the thermistor $R_H'$. The second complete circuit also can include a third measuring device $M_I'$ to determine another electrical parameter (e.g., the current) of the second complete circuit. From these measurements, the resistance of the thermistor $R_H'$ can be determined (i.e., using Ohm's law: resistance=voltage/current or $R_H'=M_H'/M_I'$).

However, when the sensing circuit is arranged as shown in FIG. 6, a leak (see $R_L'$) can develop between the first complete circuit and the second complete circuit due to the disparity in voltage between the voltage $V_{RG}$ across the sensing element $R_G'$ and the second voltage source $V_H'$. As described above, the leak can flow through impurities in the dielectric layer separating the circuits or through the dielectric itself if sufficiently heated. This leak provides a current path (see the dashed lines at $R_L'$) having parasitic resistance $R_L'$.

To reduce or prevent the current flow through the path $R_L'$, the second circuit can be interrupted, temporarily halting the flow of current from the second voltage source $V_H'$. The second circuit, and hence the measurement devices $M_H'$, $M_I'$, instead can be electrically connected to the first complete circuit (see FIG. 7). By equalizing the voltage across the sensing circuit, the leak $R_L'$ is mitigated or eliminated as indicated by the dotted lines.

The connection and disconnection of the second voltage source $V_H'$ to and from the sensing circuit is controlled by a suppression circuit I. The suppression circuit I includes circuit components capable of breaking and completing circuit paths selectively. Components of the suppression circuit I complete and break the current path according to a duty cycle of the suppression circuit I. In general, the cycle time of the suppression circuit I is programmed to be sufficiently faster than the thermal time constant of the thermistor $R_H'$ to maintain the thermistor $R_H'$ at a generally constant temperature (e.g., plus or minus a few degrees). The cycle time also is sufficiently slow to enable the necessary measurements of $R_G'$ to be taken. Typically, the cycle time is in the range of a few milliseconds.

In the example shown, the suppression circuit I includes a two-way switch (e.g., a Single Pole, Double Throw switch) S and a switch manager $C_L$. The switch manager $C_L$ controls when the switch S moves from a first position, in which the switch S completes the current path to the second voltage source $V_H'$, to a second position, in which the switch S interrupts the current path to the second voltage source $V_H'$. For example, the switch manager $C_L$ can be configured to flip the switch S about 500 times per second.

In general, the resistance of the sensor element $R_G'$ is proportional to the constituent present in the surrounding environment. The resistance of the sensor element $R_G'$ can be determined by measuring the voltage $V_{RG}$ across the sensor $R_G'$ at $M_G'$ and dividing the result by a measured current $I_R$ running through the sensor $R_G'$ (i.e., $R_G'=V_{RG}/I_R$).

To measure the current $I_R$ flowing through the sensor element $R_G'$ accurately, no significant current can flow from the first complete circuit to the thermistor $R_H'$. In an embodiment, the sensing circuit includes a buffer B to drive the thermistor $R_H'$ to a voltage of $V_{RG}$ without significant current flowing to the thermistor $R_H'$. When the switch S electrically connects the thermistor $R_H'$ to the first complete circuit via the buffer B, therefore, the voltage across the thermistor $R_H'$ and the voltage across the sensor element $R_G'$ are about the same.

Figure 8:
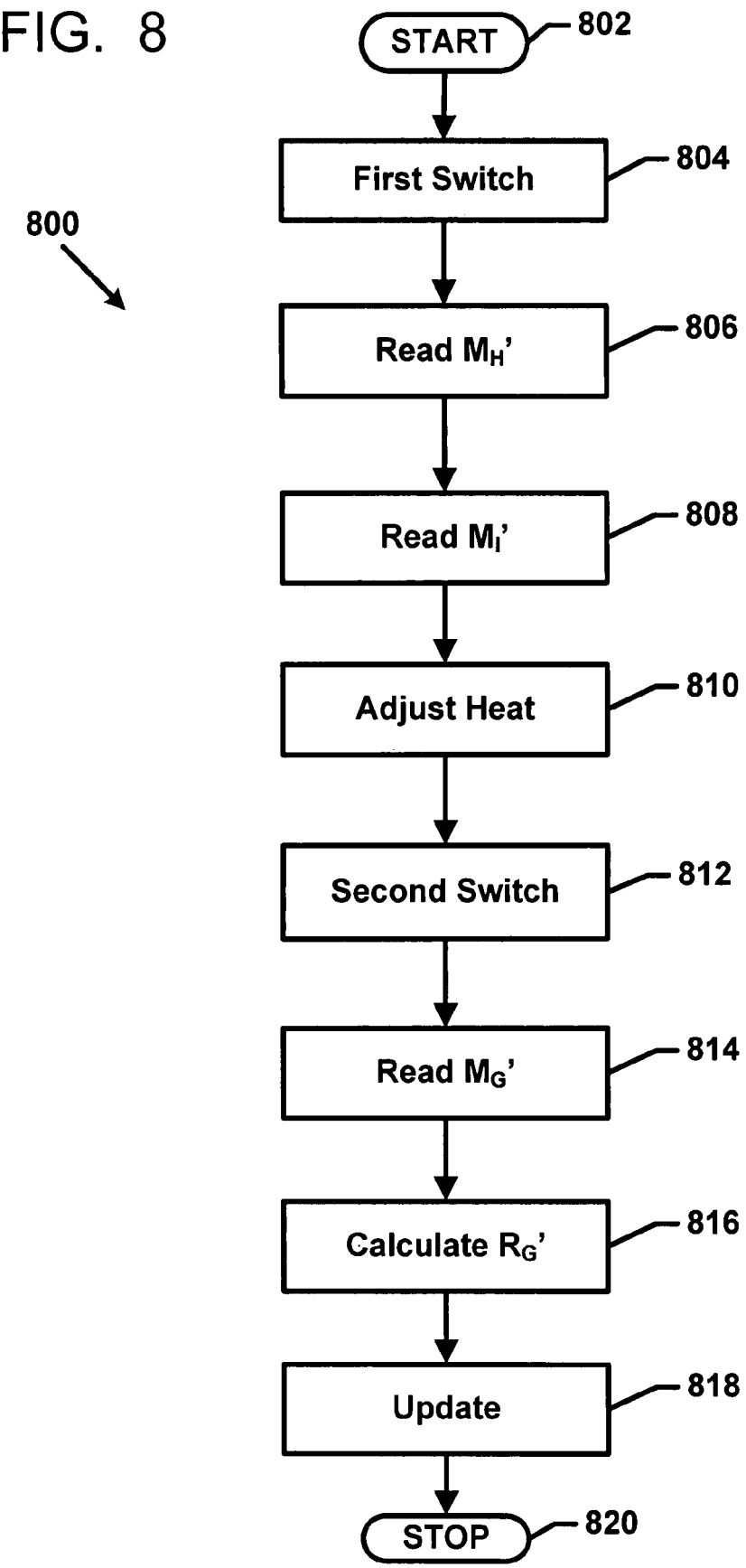
FIG. 8 is a flowchart illustrating an exemplary operation flow of a detecting process to determine whether a constituent is present in a sample in accordance with the principles of the present invention.
Figure 9:
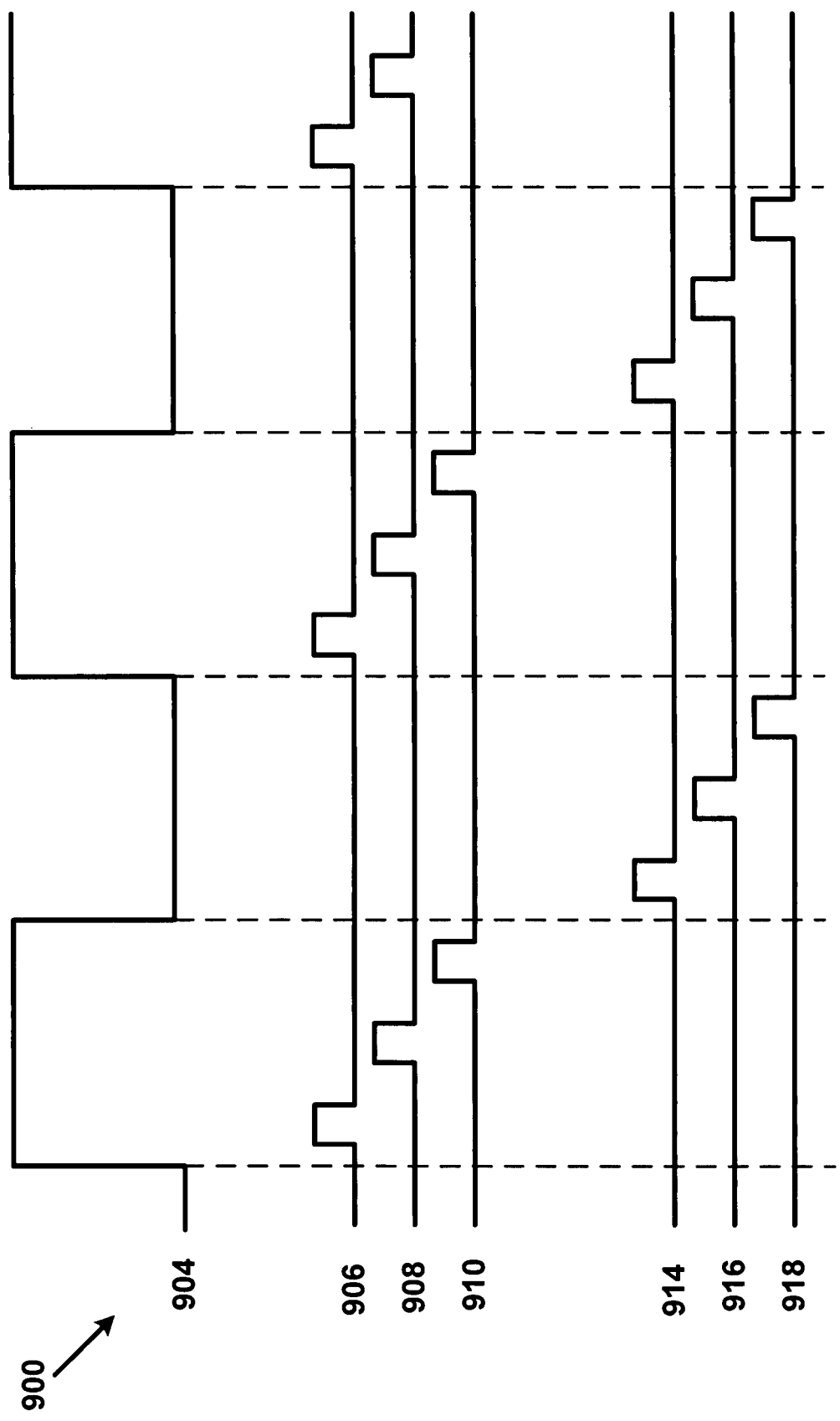
FIG. 9 is a timing diagram illustrating the switching between the arrangements shown in FIGS. 6 and 7 in accordance with the principles of the present invention.
Figure 10A:
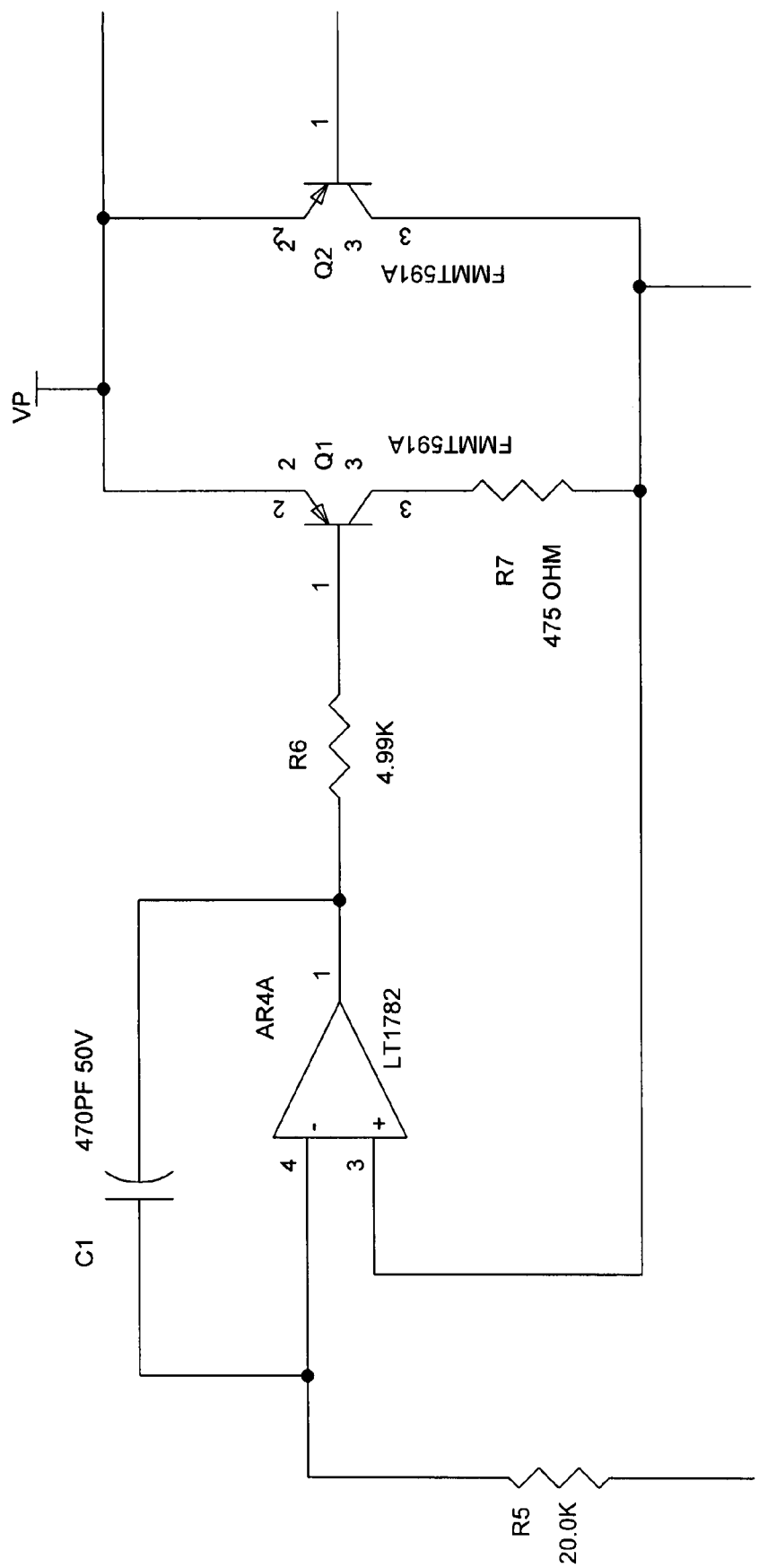
FIG. 10 is an exemplary wiring diagram of a solid-state sensor in combination with a computing device in accordance with the principles of the present invention.
Figure 10B:
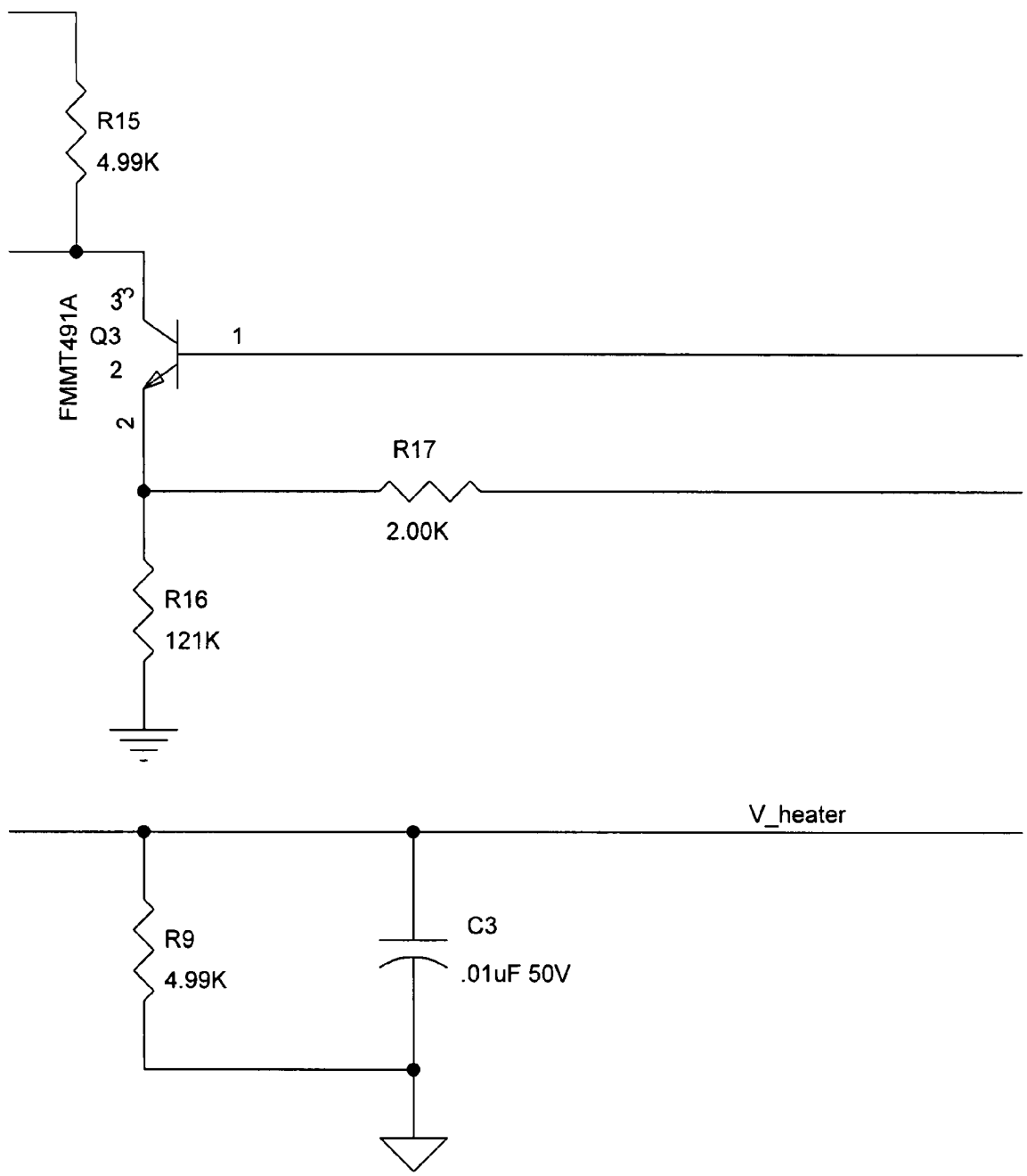
Figure 10C:
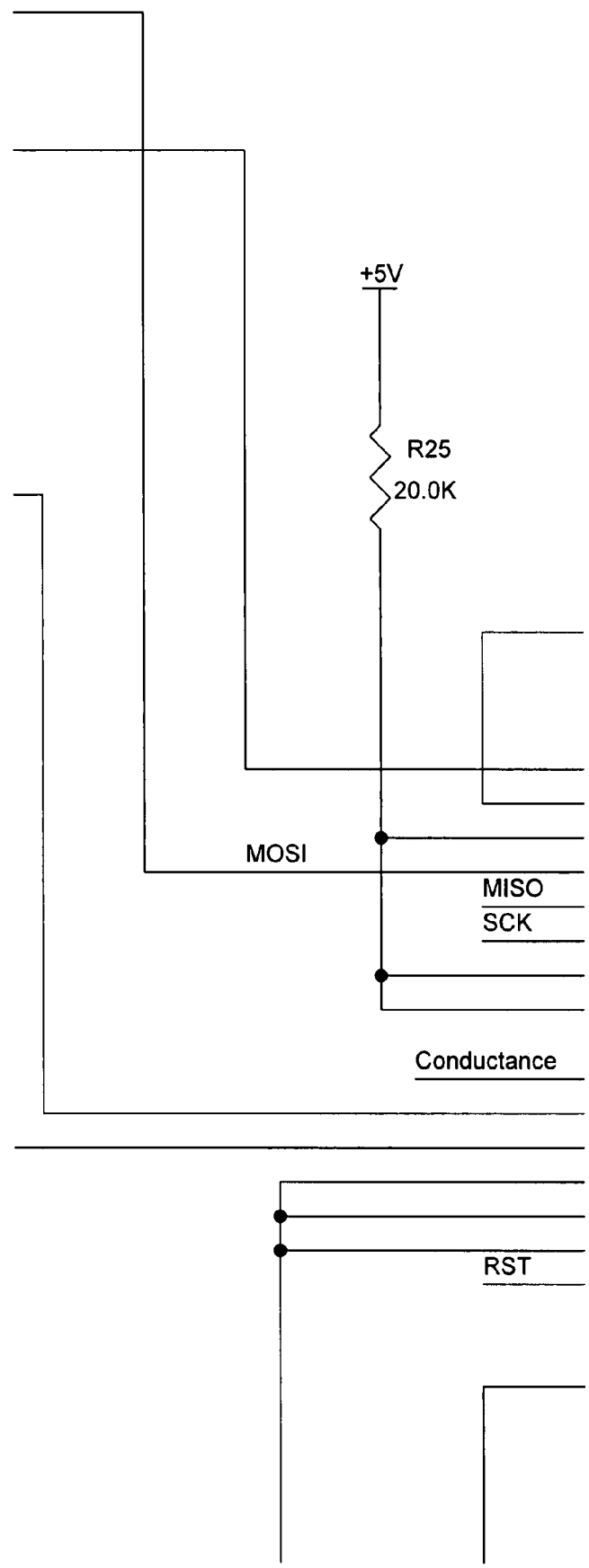
Figure 10D:
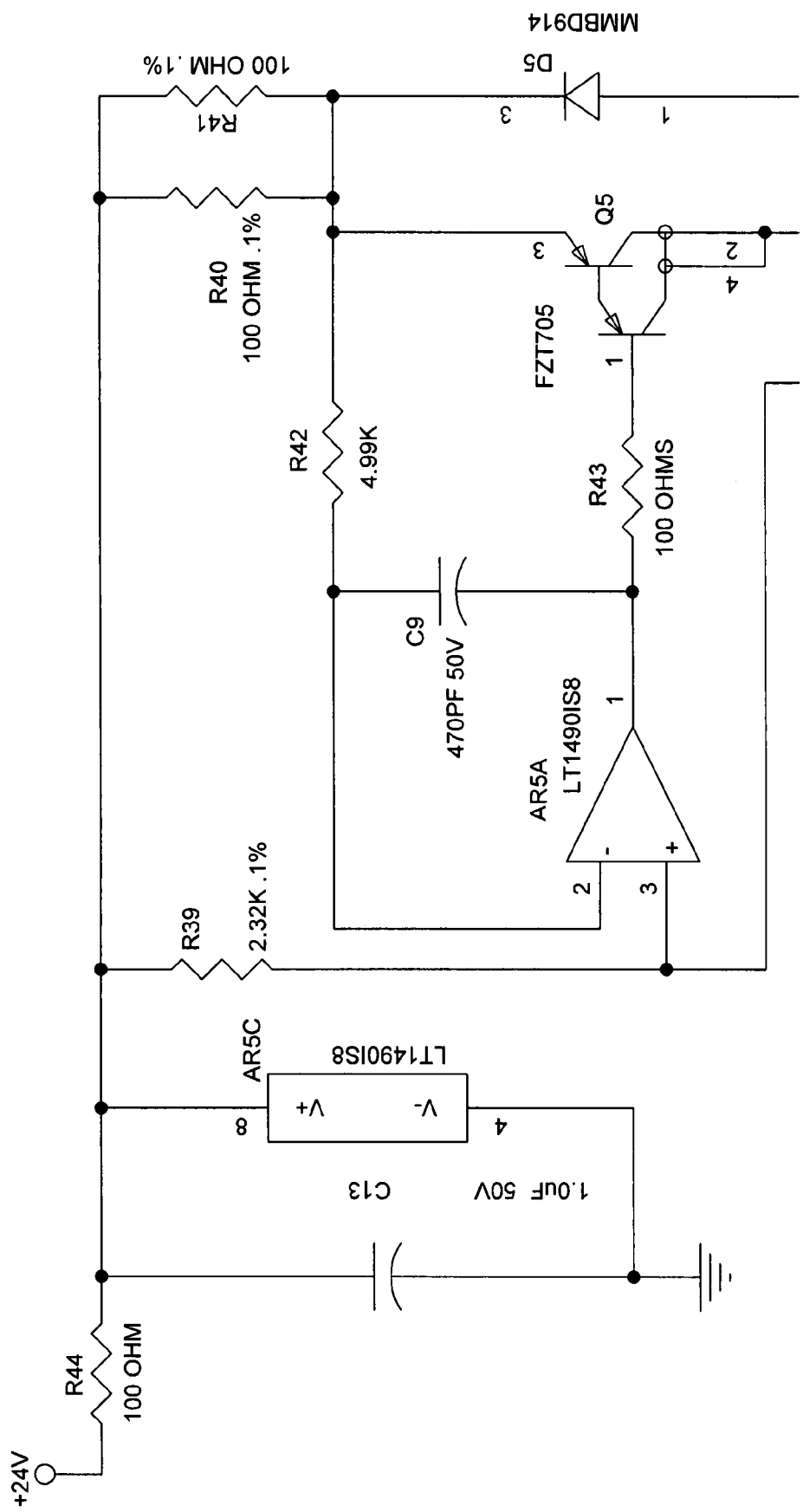
Figure 10E:
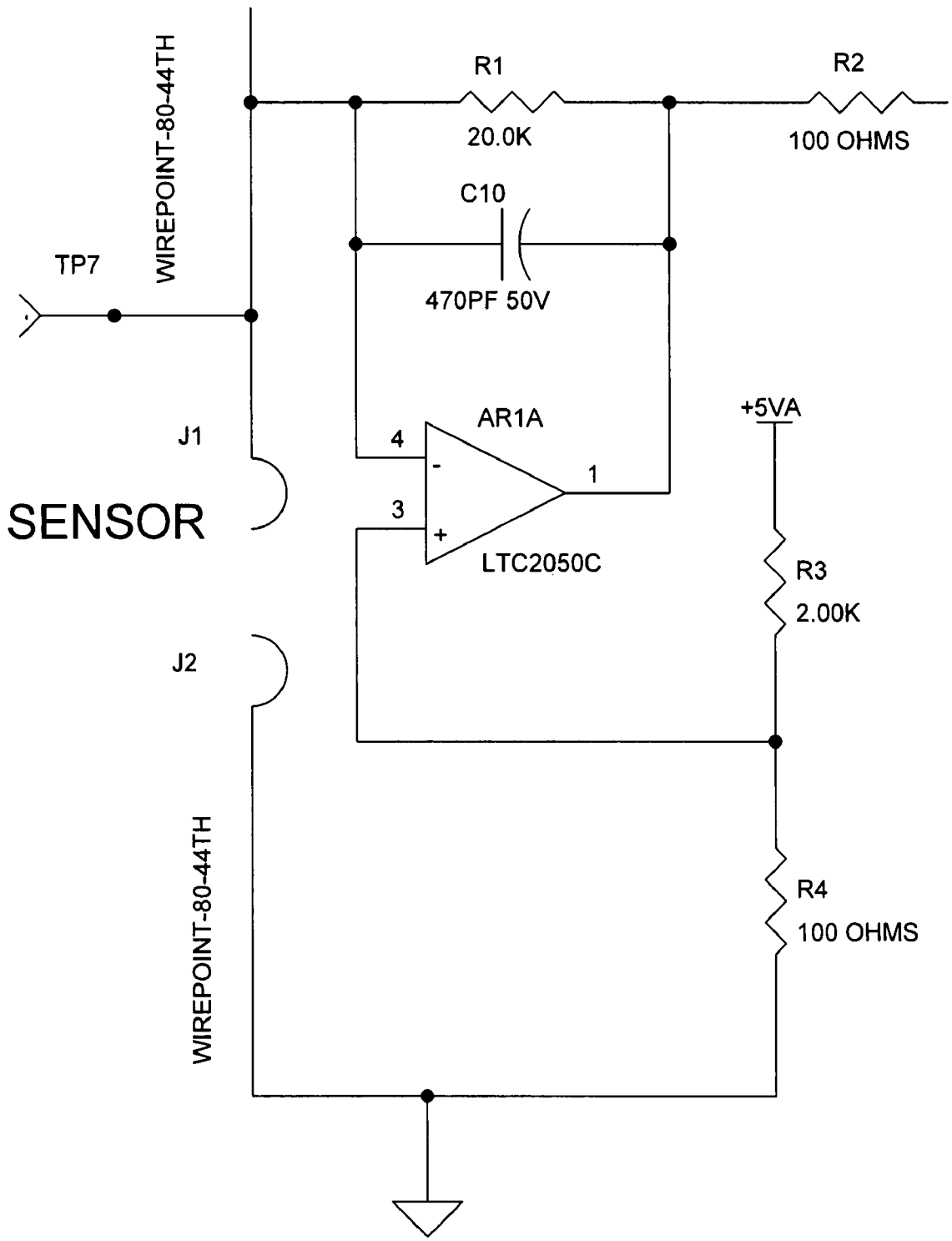
Figure 10G:
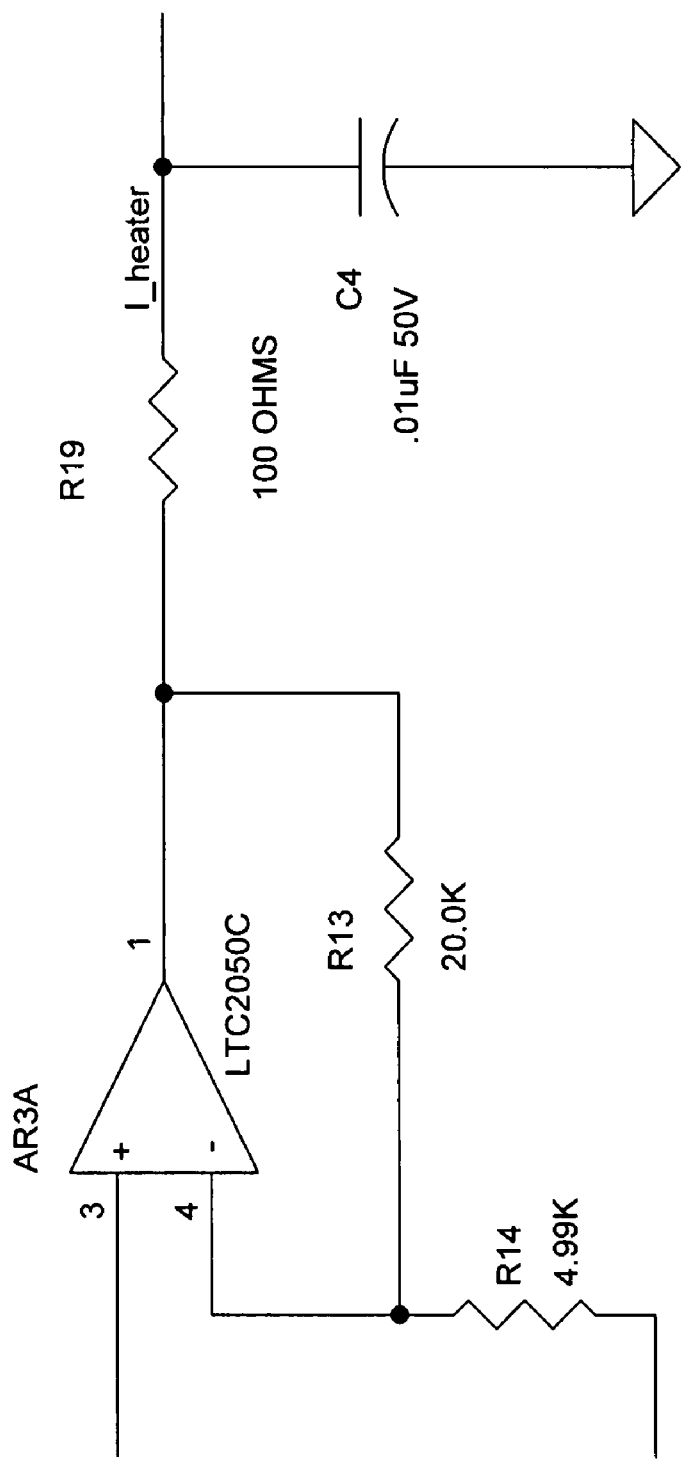
Figure 10H:
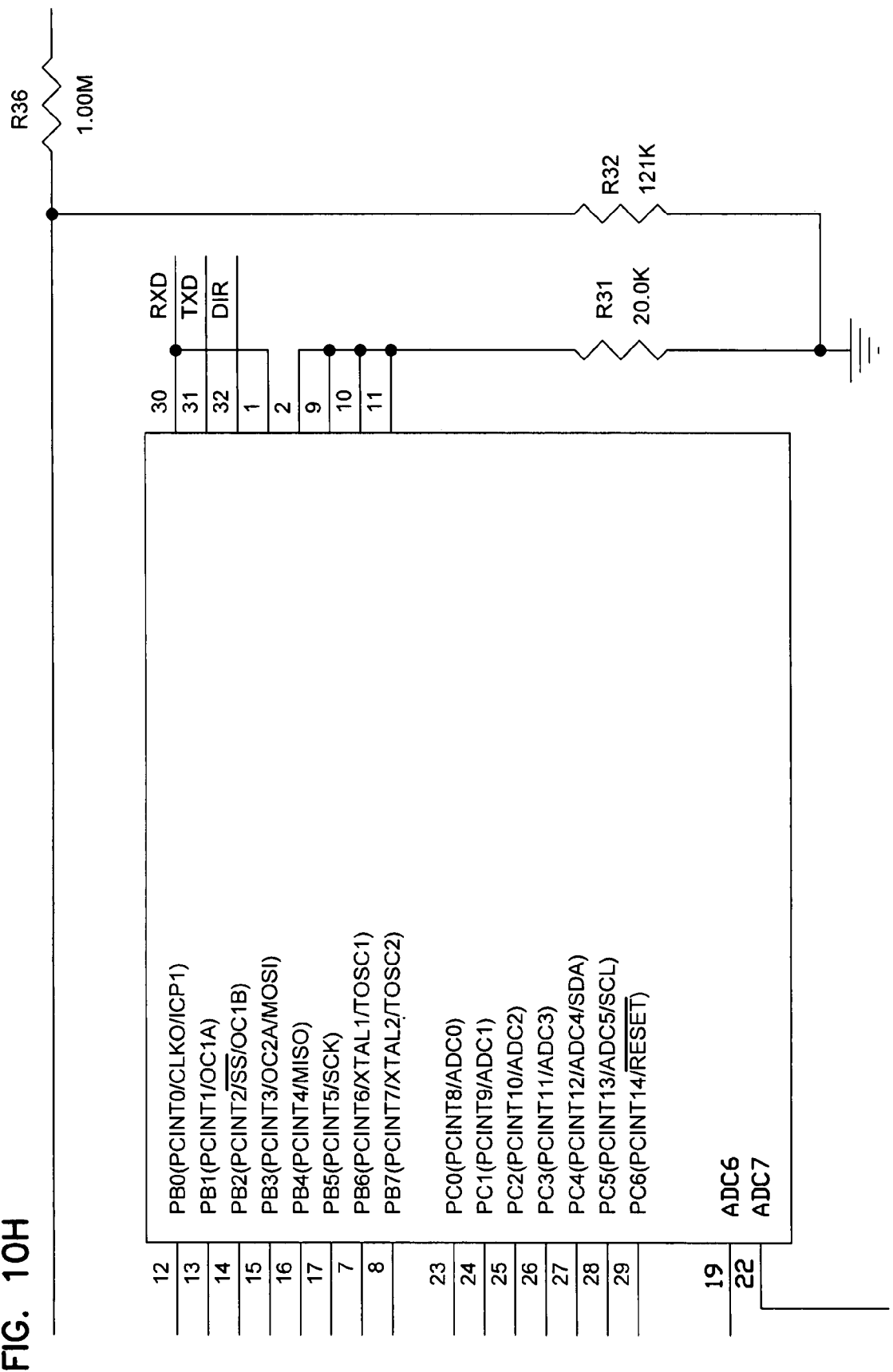
Figure 10I:
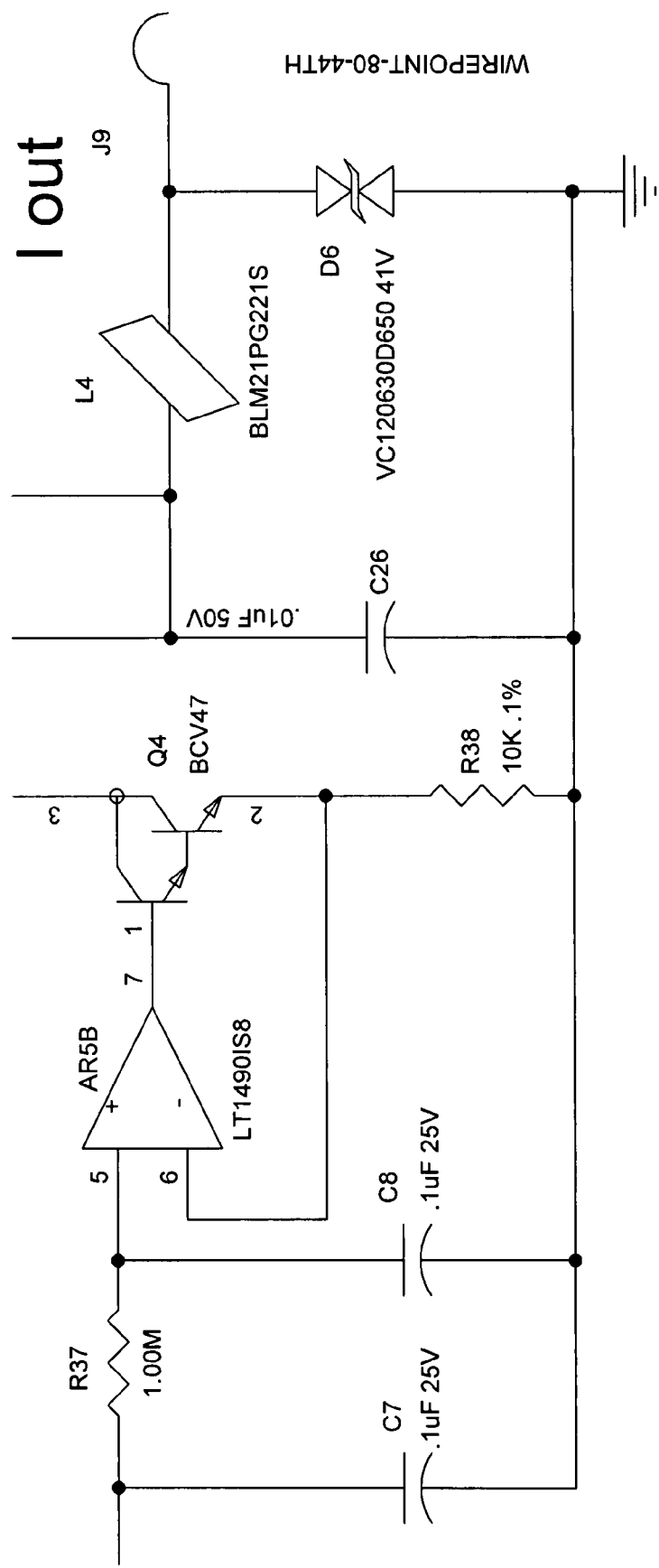
Figure 10J:
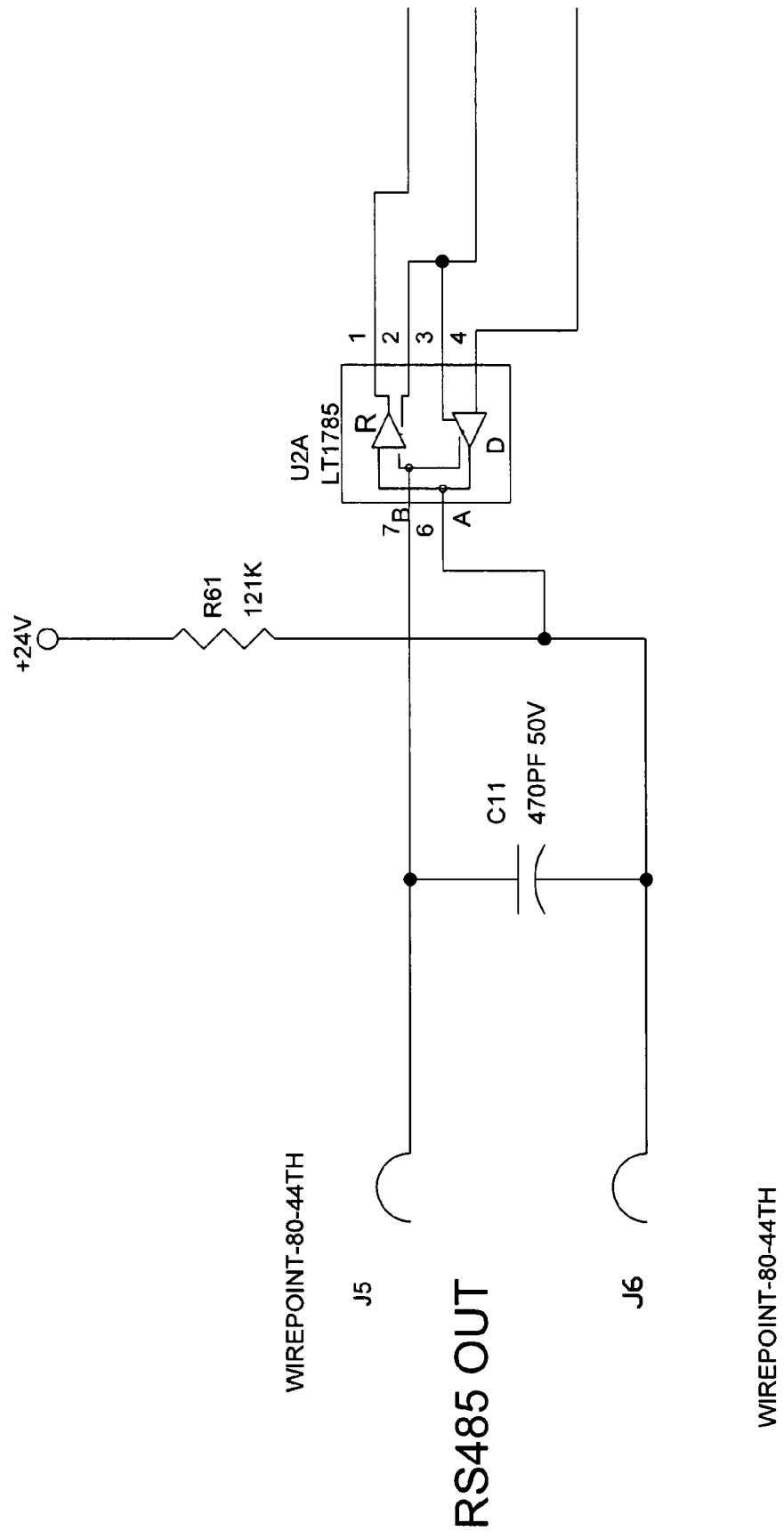
Figure 10K:
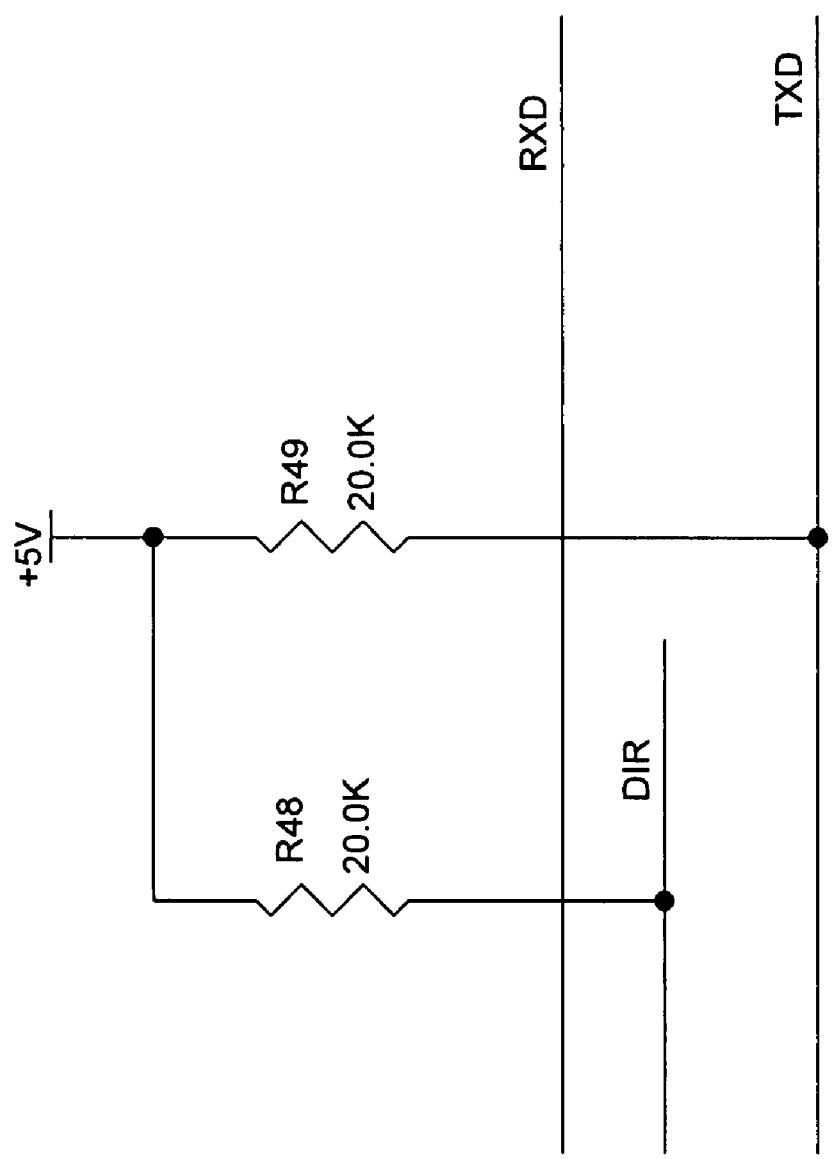
Figure 10L:
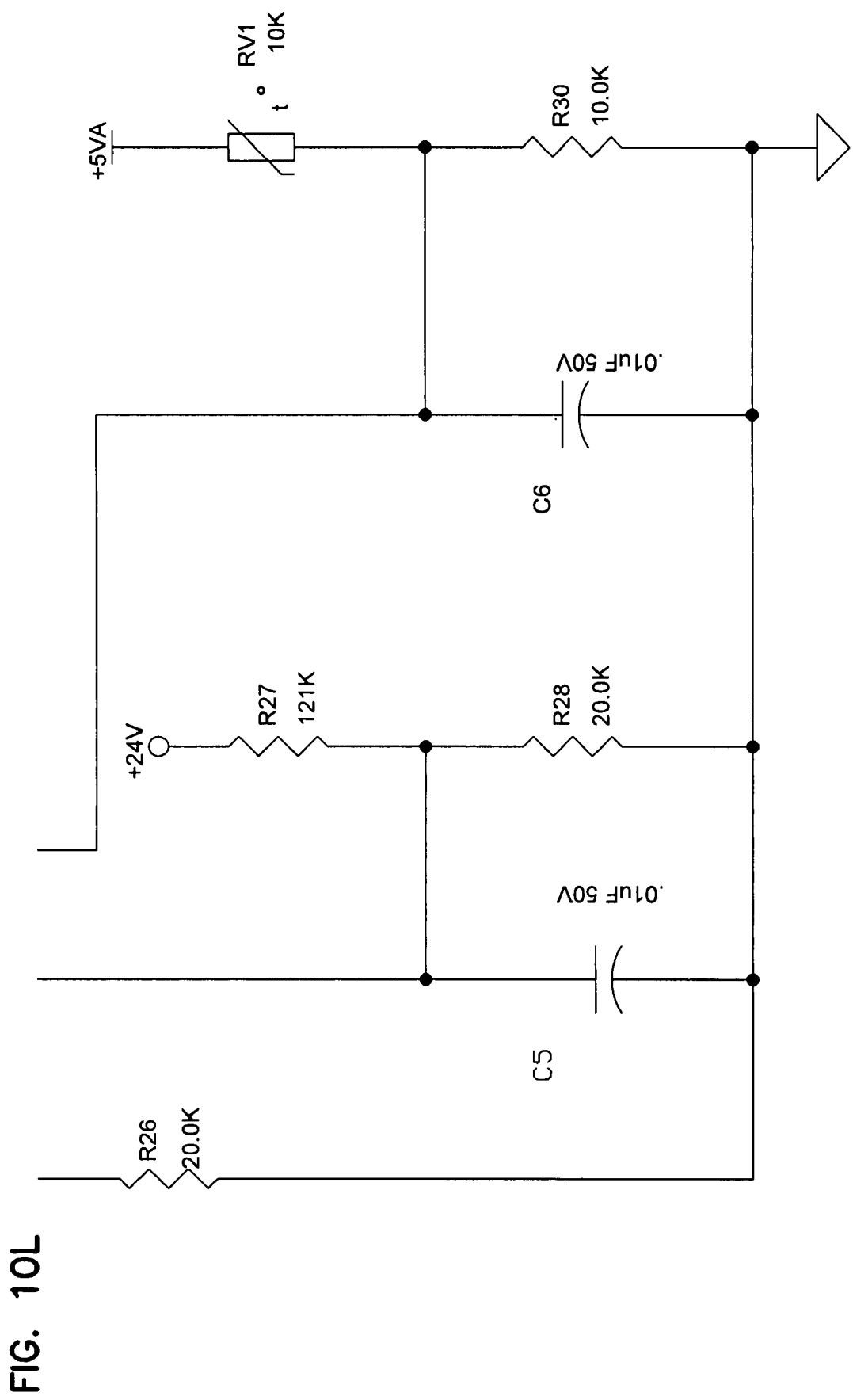
Figure 10N:
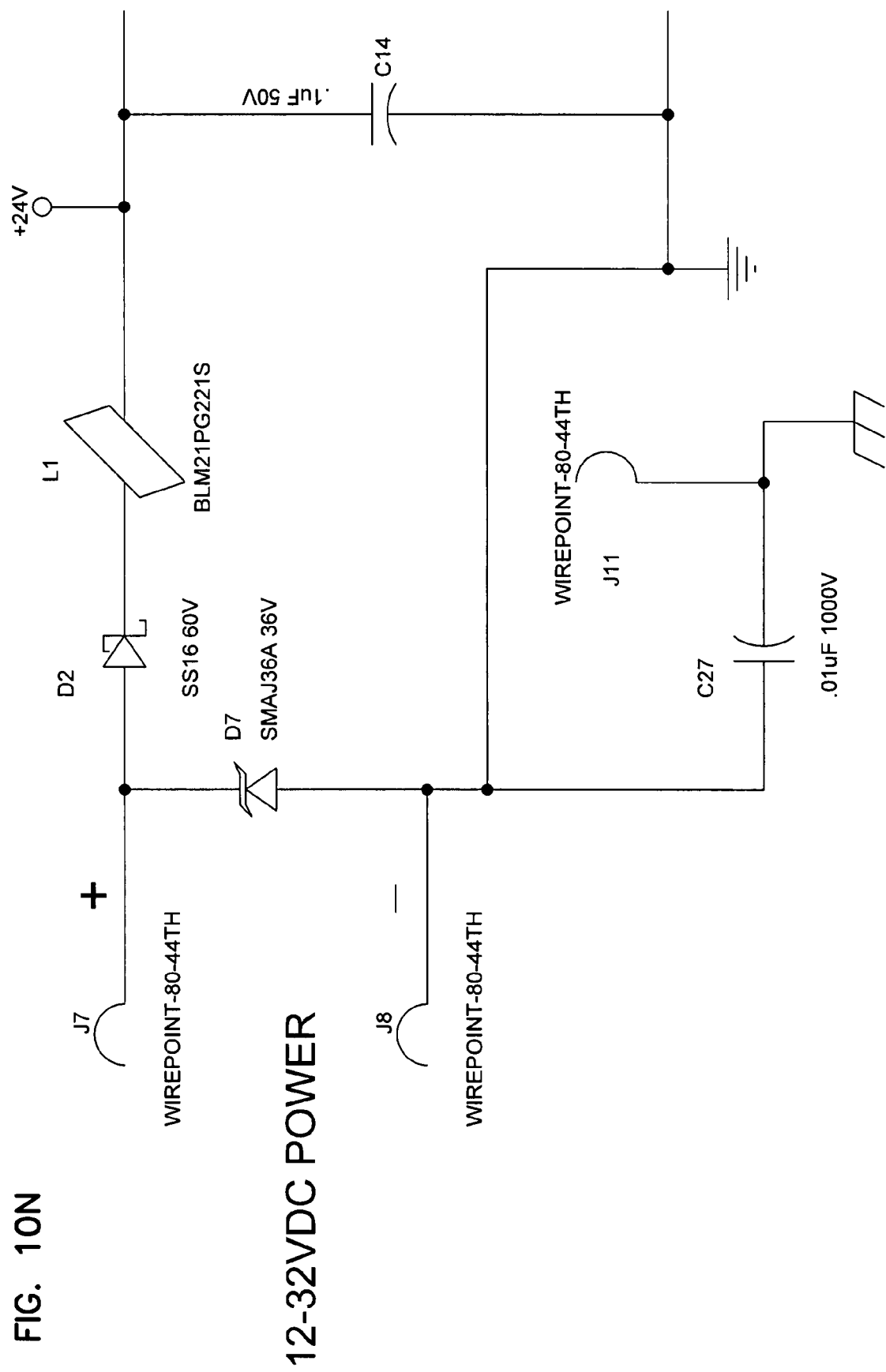
Figure 100:
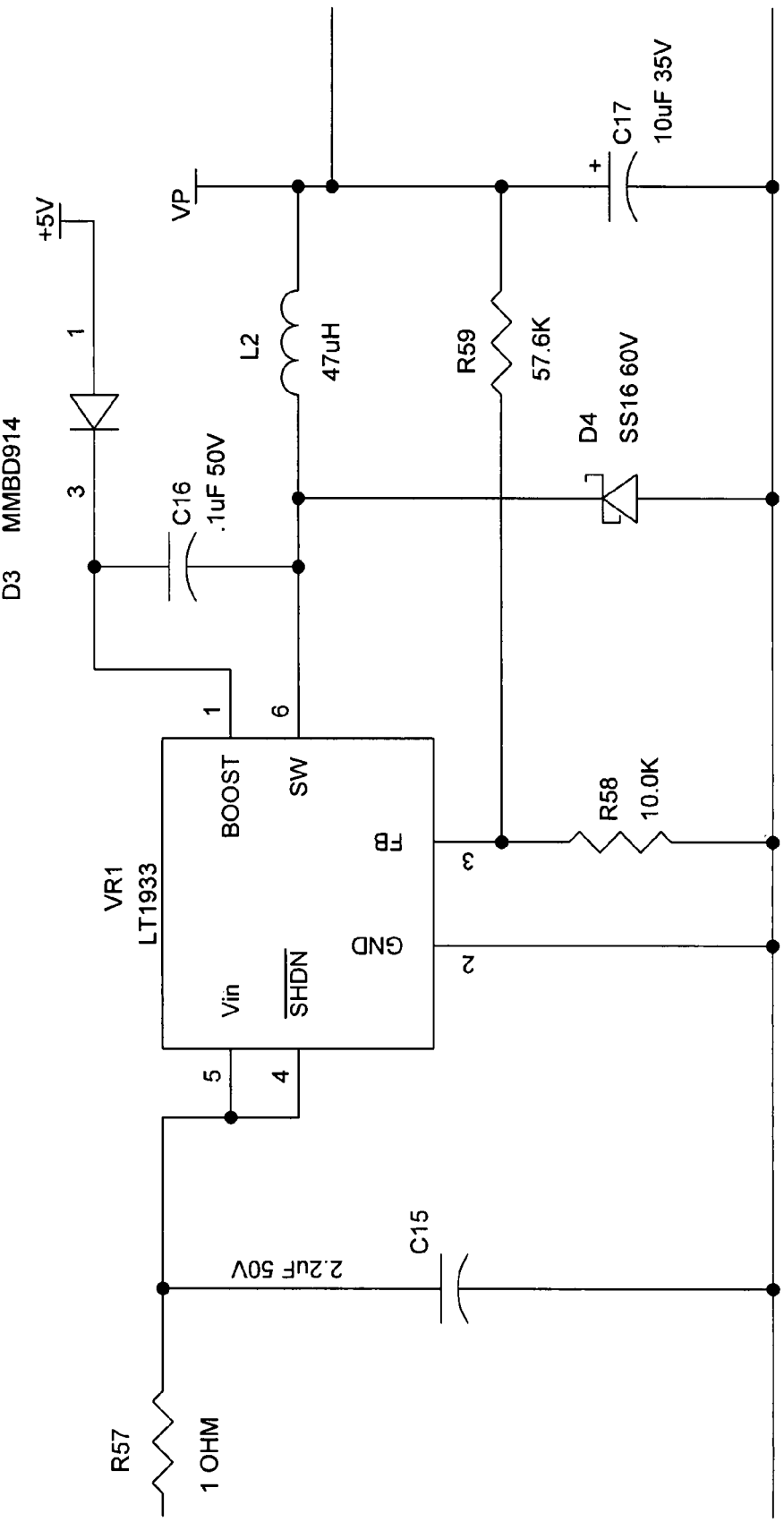
Figure 10P:
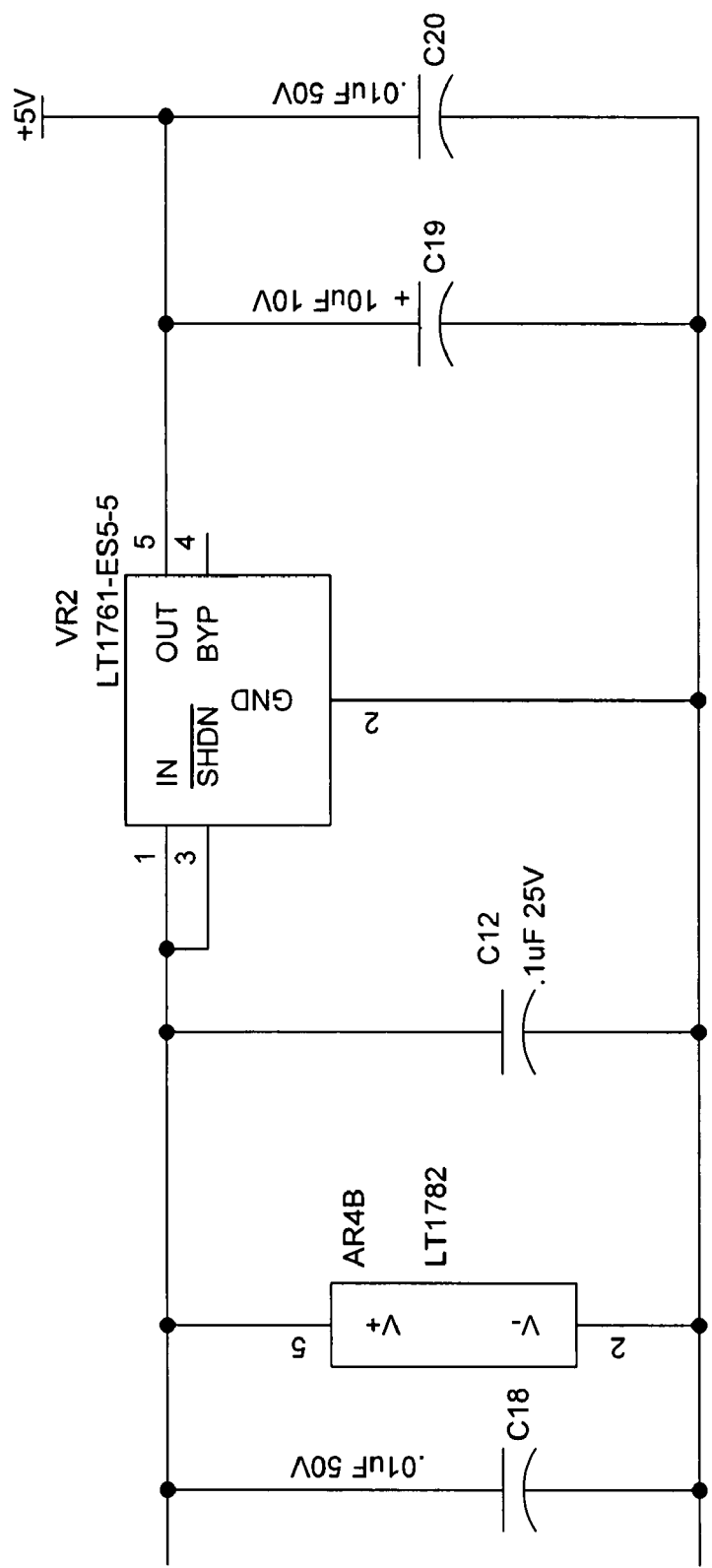
Figure 10Q:
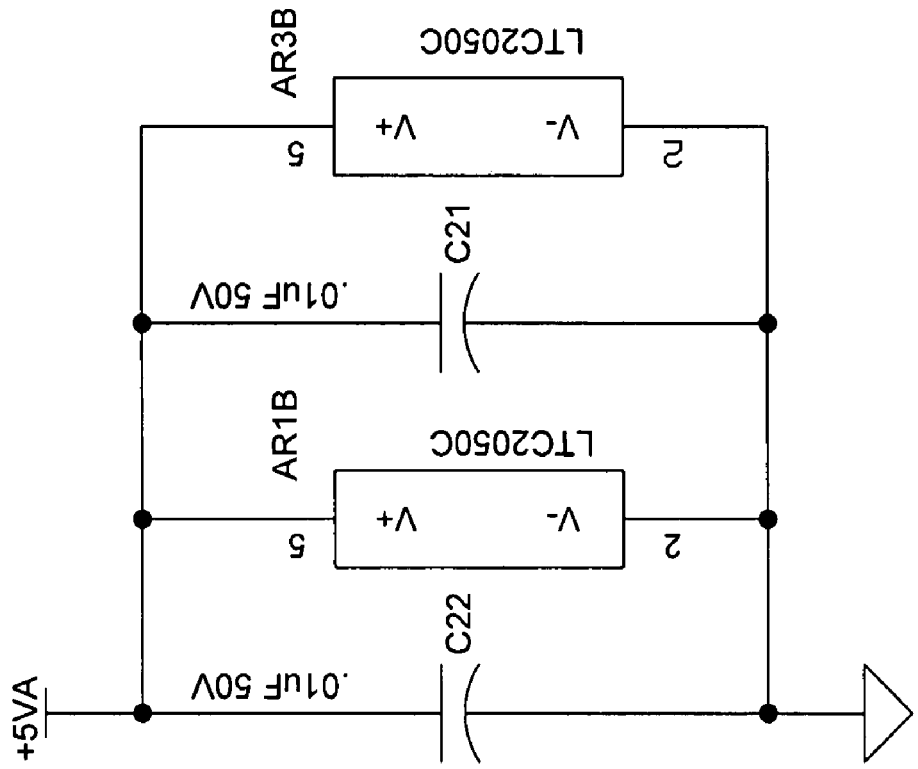
Figure 10R:
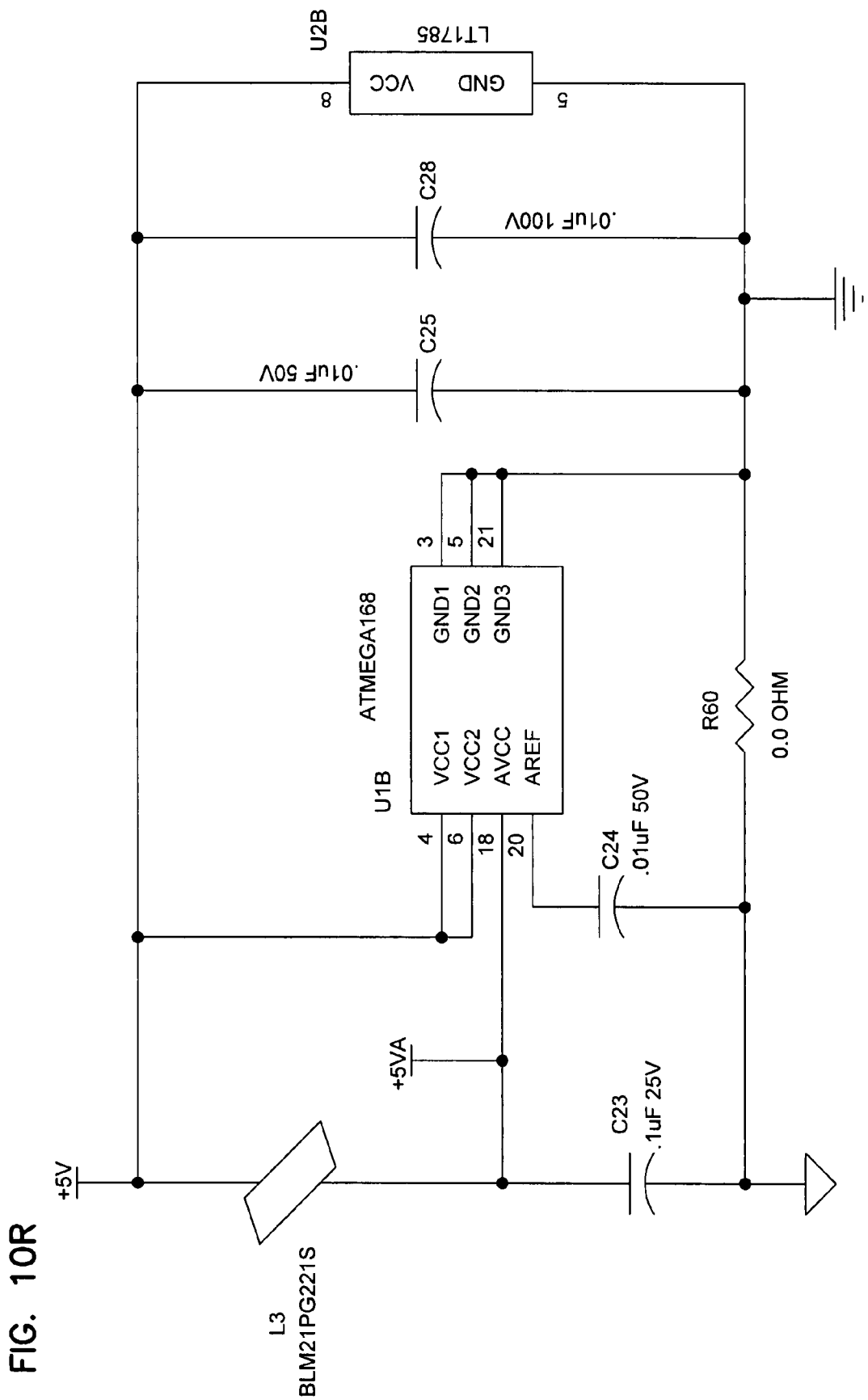

Referring now to FIGS. 8-10, in use, the sensing circuit periodically flips between the circuit arrangement shown in FIG. 6 and the circuit arrangement shown in FIG. 7. FIG. 8 is a flowchart illustrating an exemplary operational flow of a detection process 800 to determine whether a constituent is present in a sample in accordance with the principles of the present invention. FIG. 9 is a timing diagram 900 illustrating the activities of the sensing circuit in each circuit arrangement (see FIGS. 6 and 7). The timing cycle of each operation in detection process 800 is illustrated in FIG. 9.

The detecting process 800 initializes and begins at a start module 802 and proceeds to a first switch operation 804. The first switch operation 804 electrically completes the heating circuit HC to electrically connect the thermistor $R_H'$ to the second power source $V_H'$ (see FIG. 6). The timing diagram 900 illustrates a first cycle 904 according to which the switch S flips between the first position, shown in FIG. 6, and the second position, shown in FIG. 7.

A first read operation 806 determines the voltage $M_H'$ across the thermistor $R_H'$, e.g., by reading a voltmeter. A second read operation 808 measures the current $M_I'$ flowing through the heating circuit HC. From these measurements $M_H'$, $M_I'$, an adjust operation 810 can calculate the resistance (and hence the heat) of the thermistor $R_H'$. The adjust operation 810 modulates the amplitude or timing of the voltage applied to the thermistor $R_H'$ to increase or decrease the production of heat. For example, the adjust operation 810 maintains the sensing circuit at a consistent temperature, e.g., at about 300° C.

Examples of the implementation cycles 906, 908, 910 of these operations 806, 808, 810, respectively, are shown in FIG. 9 beneath the first cycle 904. As shown, these operations 806, 808, 810 are timed to occur while the switch S is arranged in the first position and the second power source $V_H'$ is electrically coupled to the thermistor $R_H'$.

A second switch operation 812 disconnects the thermistor $R_H'$ from the second power source $V_H'$, e.g., by breaking the heating circuit HC with the electrical switch S. The second switch operation 812 also electrically connects the thermistor $R_H'$ to the first power source $V_G'$, which is powering the detection circuit SC, using the electrical switch S (see FIG. 7). The first cycle 904 of the timing diagram 900 cycles to a second position during the second switch operation 812.

A third read operation 814 measures the voltage across the sensing resistor $R_G'$, e.g., by reading a voltmeter $M_G'$. A calculate operation 816 determines the resistance of the sensing resistor $R_G'$. An update operation 818 outputs the determined value of the resistance of the sensing resistor $R_G'$. The detecting process 800 repeats as desired until completing and ending at stop module 820.

As shown in FIG. 9, these operations 814, 816, 818 can be implemented when the thermistor $R_H'$ is driven to the same voltage source $V_{RG}'$ as the sensing resistor $R_G'$ (see implementation cycles 914, 916, 918). Electrically disconnecting the second (i.e., the stronger) voltage source $V_H'$ from the sensing circuit and driving the entire sensing circuit to the same voltage source $V_{RG}'$ inhibits, or even prevents, current leaks from the heating circuit HC to the sensor circuit SC. Measuring the sensing resistance during this period increases the accuracy of the sensing circuit.

In other embodiments, however, only the read operations, 806, 808, and 814 are implemented at specific points in the switch cycle 904. In such embodiments, the adjust heat, calculate, and update operations, 810, 816, and 818 can be implemented to occur at any time independent of the switch cycle 904.

In general, the first cycle 904 of the switch S is based on the thermal time constant of the thermistor $R_H'$. In an example, the electrical switch S is controlled by a modulating signal $C_L$. In an embodiment, the modulating signal $C_L$ is transmitted from a microprocessor 1004 or other computing device to the switch 1006 of a sensing circuit 1000 (FIG. 10). The microprocessor 1004 also can be used to control the voltage sources $V_G'$, $V_H'$.

It has been shown how the objects of the invention have been achieved in a preferred embodiment. It is intended that such modifications and equivalents which will appear to one of ordinary skill in the art with the benefit of the teachings of the present invention shall be included within the scope of the claims.

What is claimed is:

1. An apparatus for sensing a constituent in an environment, said apparatus comprising:
   a. a sensor circuit having:
      i. a sensor element for sensing said constituent by presenting an electrical parameter which varies as a function of a degree of said constituent, said sensor element having a preferred operating state;
      ii. an operating state control element for maintaining said preferred operating state;
      iii. wherein a detected electrical parameter of said sensor element is subject to error resulting from a leakage of electrical current between said control element and said sensor element;
   b. a suppression circuit for inhibiting said leakage to reduce said error by equalizing voltages of the sensor element and the operating state control when the electrical parameter is measured.

2. An apparatus according to claim 1 wherein said operating state is a temperature of said sensor element and said control element is an electrical heating element for heating said sensor element to a preferred operating temperature.

3. An apparatus according to claim 2 wherein said detected electrical parameter of the sensor element is a detected resistance of the sensor element and is measured indirectly by measuring a selected one of (a) a voltage across said sensor element and (b) a current through said sensor element.

4. An apparatus according to claim 2 wherein said detected electrical parameter of the sensor element is a detected resistance of the sensor element and said suppression circuit includes circuit components to intermittently provide an operating current to said heating element and to measure said detected resistance when no operating current is provided to said heating element.

5. An apparatus according to claim 4, wherein said suppression circuit comprises a switch configured to couple the heating circuit alternately to a fixed voltage source and to a variable voltage source.

6. An apparatus according to claim 5, wherein said fixed voltage source is connected to the sensor element.

7. An apparatus according to claim 2 wherein:
   a. said detected electrical parameter of the sensor element is a detected resistance of the sensor element;
   b. said suppression circuit includes circuit components for, at least intermittently, assuring a voltage drop across said heating element approximates a voltage drop across said sensor element; and
   c. said detected resistance is measured indirectly by measuring said voltage drop across said sensor element.

8. An apparatus according to claim 2 wherein said sensing element is a solid state sensing element with variable electrical resistance in response to concentrations of a gas in ambient atmosphere.

9. An apparatus according to claim 2 wherein said heating element is an electrically resistive heating element in close proximity to said sensing element to conductively heat said sensing element in response to heating of said heating element in response to electrical current flow through said heating element.

10. A method of measuring a gas with a sensor having a detection circuit and a heating circuit, the method comprising:
    connecting the detection circuit to a fixed voltage source, the detection circuit having an electrical parameter which varies as a function of a concentration of said gas, the detection circuit being configured to operate when a temperature of the detection circuit is maintained at a predetermined temperature;
    connecting the heater circuit to a variable voltage source to generate heat to maintain the temperature of the detection circuit at the predetermined temperature;
    periodically disconnecting the variable voltage source from the heater circuit and connecting the fixed voltage source to the heater circuit; and
    measuring the electrical parameter of the detection circuit when the fixed voltage source is connected to the heater circuit.

11. The method of claim 10, wherein periodically disconnecting the variable voltage source comprises disconnecting the variable voltage source according to a duty cycle.

12. The method of claim 11, wherein a frequency of the duty cycle is about 500 hertz.

13. The method of claim 10, wherein measuring the electrical parameter of the detection circuit comprises measuring a current of the detection circuit.

14. The method of claim 10, wherein measuring the electrical parameter of the detection circuit comprises measuring a voltage of the detection circuit.

15. The method of claim 10, wherein connecting the heater circuit to the variable voltage source maintains the temperature of the detection circuit at about 300.degree. C.

16. An apparatus for sensing a subject of interest in an environment, said apparatus comprising:
    a sensor element having a resistance that varies in response to exposure to the subject of interest, the sensor element being configured to receive a sample and to output an electrical signal affected by the resistance of the sensor element,
    a controller configured to maintain an operating property of the sensor element;
    a first voltage source configured to drive the sensor element to a first voltage;
    a second voltage source configured to drive the controller to a second voltage, the second voltage being significantly greater than the first voltage; and
    an suppression element configured to disconnect the controller from the second voltage source and to drive the controller to about the first voltage.

17. The apparatus of claim 16, wherein the controller is a heater configured to maintain an operating temperature of the sensor element.

18. The apparatus of claim 16, wherein the suppression element is an electrical switch configured to electrically connect the controller to the first voltage source.

19. The apparatus of claim 16, further comprising a measurement unit configured to receive the electrical signal output from the sensor element and to determine an amount of the subject of interest present in the sample by analyzing the electrical signal.

* * * * *